United States Patent
Shi et al.

(10) Patent No.: US 10,947,225 B2
(45) Date of Patent: Mar. 16, 2021

(54) PHOSPHOTIDYLINOSITOL 3-KINASE INHIBITORS

(71) Applicant: Emory University, Atlanta, GA (US)

(72) Inventors: Qi Shi, Edison, NJ (US); Thomas Kaiser, Atlanta, GA (US); John DiRaddo, Fairport, NY (US); James Snyder, Atlanta, GA (US); Dennis Liotta, Atlanta, GA (US); Zackery Dentmon, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/301,421

(22) PCT Filed: May 11, 2017

(86) PCT No.: PCT/US2017/032215
§ 371 (c)(1),
(2) Date: Nov. 13, 2018

(87) PCT Pub. No.: WO2017/197151
PCT Pub. Date: Nov. 16, 2017

(65) Prior Publication Data
US 2019/0202826 A1    Jul. 4, 2019

Related U.S. Application Data

(60) Provisional application No. 62/478,206, filed on Mar. 29, 2017, provisional application No. 62/334,896, filed on May 11, 2016.

(51) Int. Cl.
*C07D 471/04* (2006.01)
*A61K 31/4745* (2006.01)

(52) U.S. Cl.
CPC ........ *C07D 471/04* (2013.01); *A61K 31/4745* (2013.01)

(58) Field of Classification Search
CPC .................................................. C07D 471/04
See application file for complete search history.

(56) References Cited

U.S. PATENT DOCUMENTS

| 2014/0256717 A1 | 9/2014 | Fernandez |
| 2015/0290207 A1 | 10/2015 | Kutok |

FOREIGN PATENT DOCUMENTS

| EP | 1277754 | 1/2003 |
| KR | 20130102814 | 9/2013 |
| KR | 20150012788 | 2/2015 |
| WO | 2007127183 | 11/2007 |
| WO | 2008014219 | 1/2008 |
| WO | 2010100144 | 9/2010 |

OTHER PUBLICATIONS

Akinleye et al., Phosphatidylinositol 3-kinase (PI3K) inhibitors as cancer therapeutics; Journal of Hematology & Oncology 2013, 6:88.
Glauer et al., A novel selective small-molecule PI3K inhibitor is effective against human multiple myeloma in vitro and in vivo, Blood Cancer Journal, 2013, 3, e141.
Graupera et al., Angiogenesis selectively requires the p110alpha isoform of PI3K to control endothelial cell migration, Nature letters, 2008, vol. 453, pp. 662-666.
Jeong et al., Selectivity enhancement arising from interaction at the PI3K unique pocket, Chemmedchem Communications, 2012, 7, 1379-1383.
Jung et al., Suppression of tumor proliferation and angiogenesis of hepatocellular carcinoma by HS-104, a novel phosphoinositide 3-kinase inhibitor, Cancer Letters, 2013, 328, 176-187.
Kim et al., Design and Synthesis of imidazopyridine analogues as inhibitors of phosphoinositide 3-kinase signaling and angiogenesis, Journal of Medicinal Chemistry, 2011, 54, 2455-2466.
Shi et al., Design and validation of FRESH, a drug discovery paradigm resting on robust chemical synthesis, ACS Medicinal Chemistry Letters, 2015, 6, 518-522.
Ward et al., Isoform-specific phosphoinositide 3-kinase inhibitors as therapeutic agents, Current Opinion in Pharmacology, 2003, 3, 426-434.
Arjumond et al. Phosphatidyl inositol-3 kinase (PIK3CA) E545K mutation confers cisplatin resistance and a migratory phenotype in cervical cancer cells, Oncotarget. 2016, 7(50), 82424-82439.
Janku et al., PIK3CA Mutations in Advanced Cancers: Characteristics and Outcomes, Oncotarget. 2012, 3(12), 1566-1575.
Jiang et al., The PIK3CA E542K and E545K mutations promote glycolysis and proliferation via induction of the β-catenin/SIRT3 signaling pathway in cervical cancer, J. Hemato.I Oncol, 2018, 11, 139.
Leontiadou et al. Insights into the mechanism of the PIK3CA E545K activating mutation using MD simulations., Sci. Rep. 2018, 8, 15544.
Liu et al. Human Tumor Mutants in the p110 alpha Subunit of PI3K, Cell Cycle. 2006, 5, 675-677.
Zardavas et al. PIK3CA mutations in breast cancer: reconciling findings from preclinical and clinical data, Breast Cancer Res. 2014, 16, 201.
Zhao et al. The E545K mutation of PIK3CA promotes gallbladder carcinoma progression through enhanced binding to EGFR, J. Exp. Clin. Cancer Res. 2016, 35, 97.

*Primary Examiner* — Brian E McDowell
(74) *Attorney, Agent, or Firm* — Emory Patent Group

(57) ABSTRACT

This disclosure relates to phosphoinositide 3-kinases (PI3Ks) inhibitors such as N-(5-(imidazo[1,2-a]pyridin-6-yl)pyridin-3-yl)sulfonamide derivatives and uses related thereto. In certain embodiments, the disclosure relates to methods of treating PI3K associated diseases or conditions comprising administering an effective amount of a compound disclosed herein to a subject in need thereof. In certain embodiments, the subject is at risk of, exhibiting symptoms of, suffering from, or diagnosed with cancer or a hematological malignancy.

19 Claims, 6 Drawing Sheets

PHOSPHOTIDYLINOSITOL 3-KINASE INHIBITORS

CROSS-REFERENCE TO RELATED APPLICATIONS

This application is the National Stage of International Application No. PCT/US2017/032215 filed May 11, 2017, which claims the benefit of U.S. Provisional Application No. 62/334,896 filed May 11, 2016 and U.S. Provisional Application No. 62/478,206 filed Mar. 29, 2017. The entirety of each of these applications is hereby incorporated by reference for all purposes.

STATEMENT REGARDING FEDERALLY SPONSORED RESEARCH OR DEVELOPMENT

This invention was made with government support under R01 CA180805-01 awarded by the National Institutes of Health. The government has certain rights in the invention.

BACKGROUND

Phosphatidylinositol 3-kinases (PI3Ks) are members of a family of kinases that phosphorylate phosphatidylinositols or phosphoinositides and are used by pathways involving growth factors, cytokines and many other extracellular signals. PI3K signaling is involved in many disease states including various types of cancer, hematologic malignancies, allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

Idelalisib is an inhibitor of PI3K delta kinase approved by the FDA, in combination with rituximab, for the treatment of patients with relapsed chronic lymphocytic leukemia (CLL). Other PI3K inhibitors are in clinical trials, such as buparlisib and alpelisib for breast cancer and duvelisib for hematologic malignancies. Some cancers are not treatable by current chemotherapy regimens. Thus, there is a need to identify improved treatment options.

Kim et al. report imidazopyridine analogues as inhibitors of phosphoinositide 3-kinase signaling and angiogenesis (Journal of Medicinal Chemistry, 2011, 54, 2455-2466). See also, Shi et al., Design and Validation of FRESH, A Drug Discovery Paradigm Resting on Robust Chemical Synthesis. ACS Medicinal Chemistry Letters 2015, 6, 518-522; Akinleye et al. Phosphatidylinositol 3-kinase (PI3K) inhibitors as cancer therapeutics J. Hematol. Oncol. 2013, 6, 88-10; and United States Patent Application 20150290207.

Of interest, PI3K γ and δ isoforms are frequently found to have copy-number-gain, amplification, and increased expression alterations in cancers like glioblastoma, neuroblastoma, ovarian, and various leukemias and lymphomas. Inhibition of PI3K γ and δ isoforms therefore represent a promising strategy for the combat of these cancers in the clinic.

References cited herein are not an admission of prior art.

SUMMARY

This disclosure relates to phosphoinositide 3-kinase (PI3Ks) inhibitors such as N-(5-(imidazo[1,2-a]pyridin-6-yl)pyridin-3-yl)sulfonamide derivatives and uses related thereto. In certain embodiments, the disclosure relates to methods of treating PI3K associated diseases or conditions comprising administering an effective amount of a compound disclosed herein to a subject in need thereof. In certain embodiments, the subject is at risk of, exhibiting symptoms of, suffering from, or diagnosed with cancer or a hematological malignancy.

In certain embodiments, the N-(5-(imidazo[1,2-a]pyridin-6-yl)pyridin-3-yl)sulfonamide derivatives are capable of selectively inhibiting one or more isoform(s) of class I PI3K.

In certain embodiments, the N-(5-(imidazo[1,2-a]pyridin-6-yl)pyridin-3-yl)sulfonamide derivatives are those having the following formula:

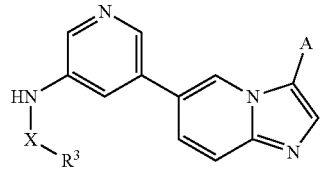

Formula I derivatives, esters, prodrugs, or salts thereof wherein the substituents are reported herein.

In certain embodiments, the derivative is any of the compounds disclosed herein optionally substituted with one or more, the same or different, substituents.

In certain embodiments, provided herein is a composition (e.g., a pharmaceutical composition) comprising a compound described herein and a pharmaceutically acceptable excipient. In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicone dioxide, titanium dioxide, talc, corn starch, carnuba wax, stearic acid, sorbic acid, magnesium stearate, calcium stearate, castor oil, mineral oil, calcium phosphate, starch, carboxymethyl ether of starch, iron oxide, triacetin, acacia gum, esters or salts thereof.

In some embodiments, provided herein is a method of inhibiting a PI3 kinase, comprising contacting the PI3 kinase with an effective amount of a compound or a pharmaceutical composition described herein. In certain embodiments, a method is provided for inhibiting a PI3 kinase wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, among others. In certain embodiments, a second therapeutic agent is administered to the subject. In one embodiment, the subject is a human.

In certain embodiments, provided herein is a method of making a compound described herein comprising mixing starting materials under conditions such that the products are formed.

In certain embodiments, provided herein is a kit comprising a compound described herein.

In some embodiments, provided herein is a use of a compound or a pharmaceutical composition described herein for the treatment of a PI3K mediated disorder in a subject.

In some embodiments, provided herein is a compound or pharmaceutical composition described herein for use in a method of treating a PI3K mediated disorder in a subject.

In some embodiments, provided herein is a use of a compound or a pharmaceutical composition described herein in the manufacture of a medicament for the treatment of a disease or disorder described herein in a subject.

DETAILED DESCRIPTION

Figure 1:
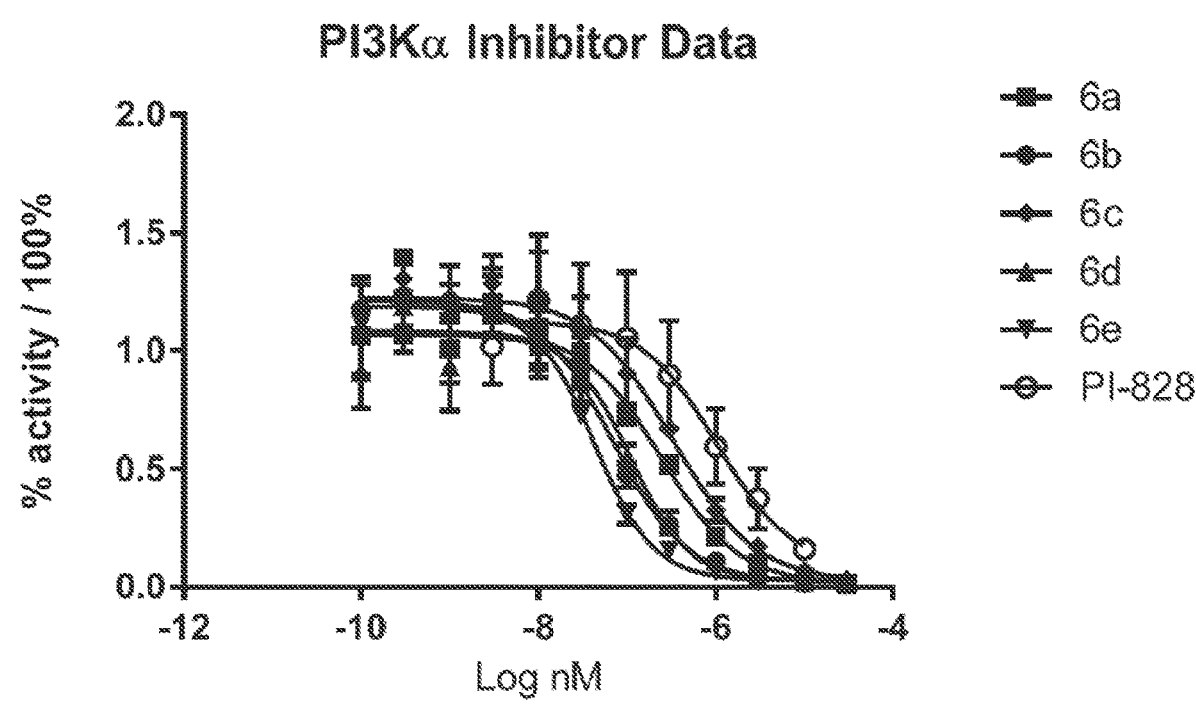
FIG. 1 shows PI3K alpha inhibitor data. The Promega V1721 ADP-Glo Lipid Kinase System was used as per the Promega technical manual. The analysis was done in triplicate on three 96-well plates. The plates were read and the data were processed with GraphPad Prism 7.0.
Figure 2:
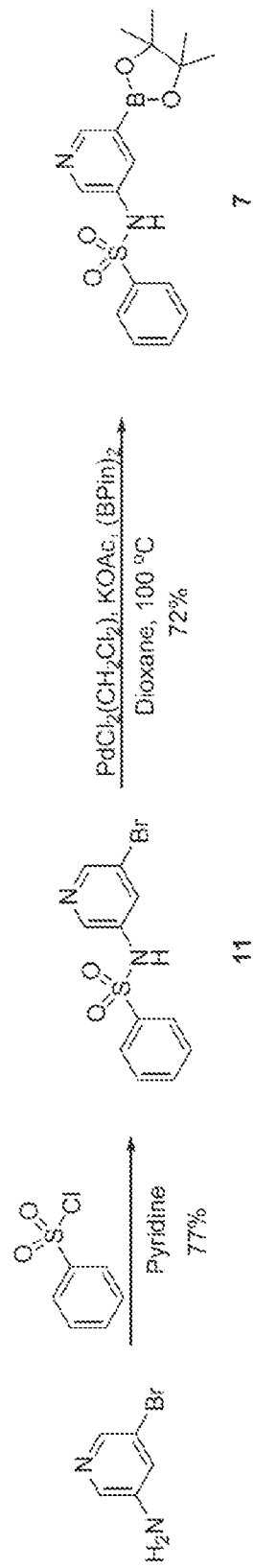
FIG. 2 illustrates the synthesis of intermediates. Compound 7 was synthesized by reacting 5-bromopyridin-3-amine with benzenesulfonyl chloride to give 11 in 77% yield. The preparation of 7 was completed by a palladium-mediated reaction to install the pinacolboronate in 72% yield.
Figure 3:
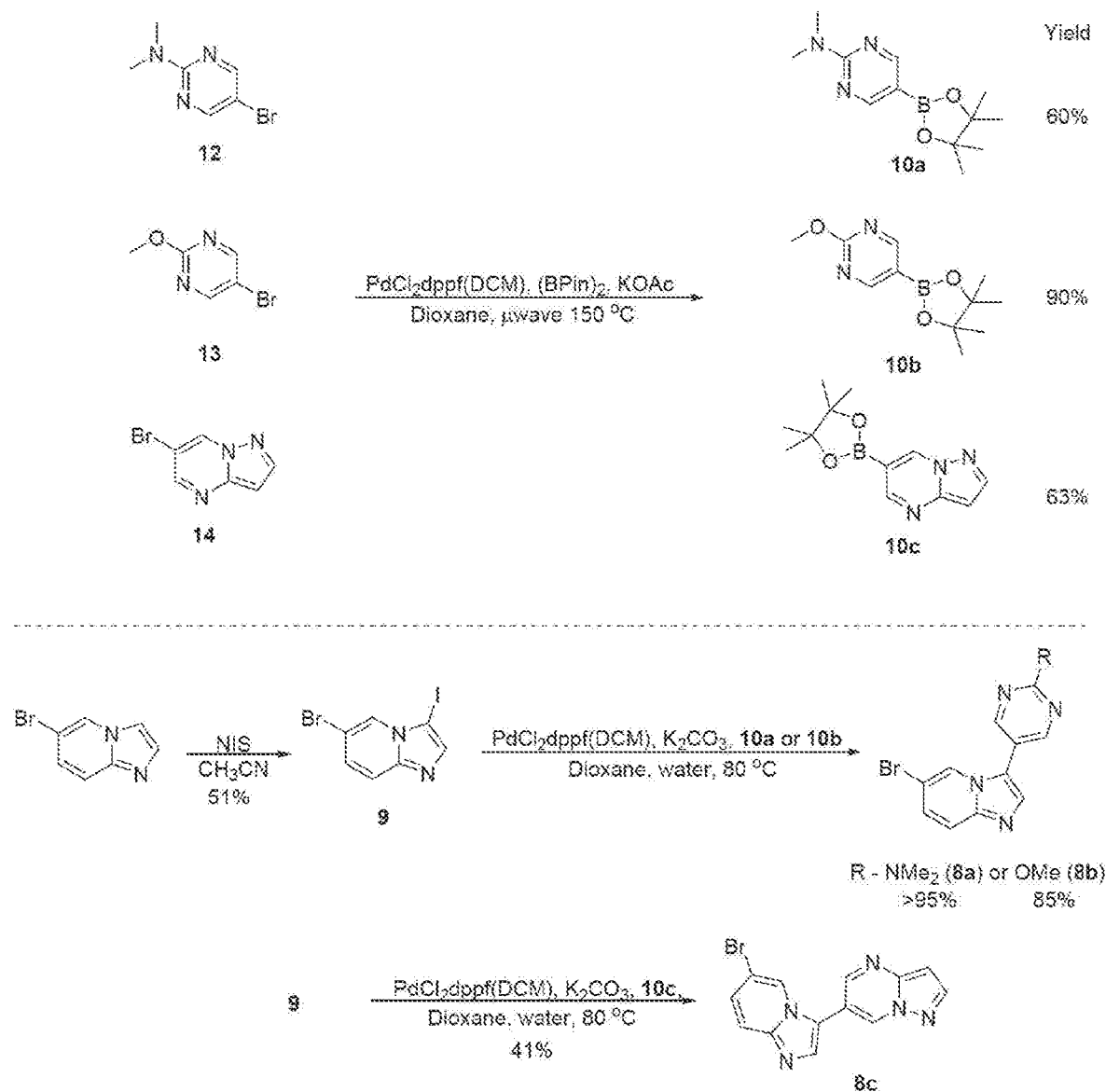
FIG. 3 illustrates the preparation of certain embodiments of the disclosure. Iodinating 6-bromoimidazo[1,2-a]pyridine with NIS gave 9 in 51% yield which was followed by elective coupling of aryl boronic esters to 9 at the iodo handle of 9. Therefore, the corresponding aryl halides, 12, 13 and 14, were used to generate the desired boronic esters 15, 16 and 17 in 60, 90 and 63% yields respectively. These boronic esters were then coupled with 4 via Suzuki reaction to give the desired 8a, 8b and 8c in 41 to >95% yield.
Figure 4:
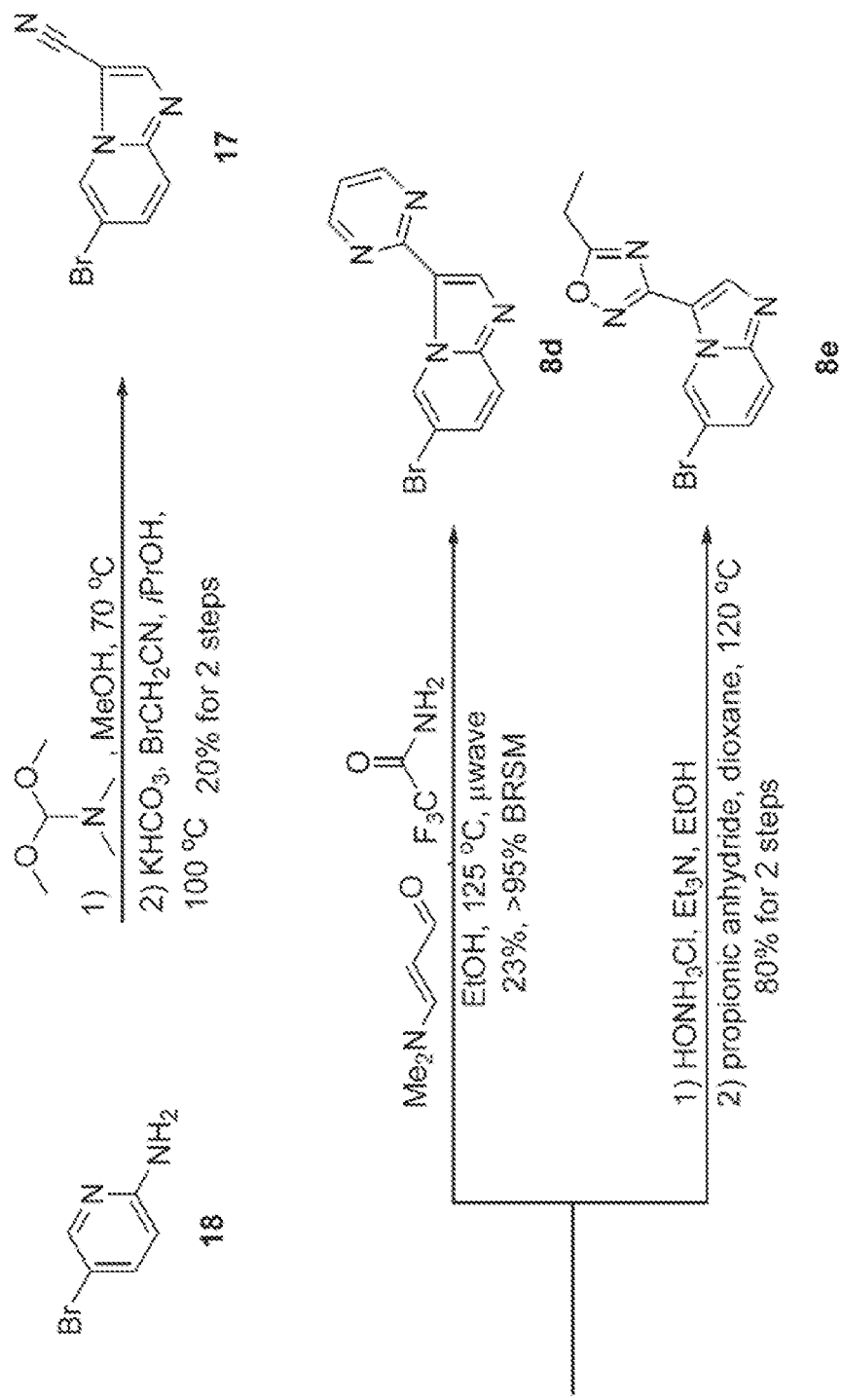
FIG. 4 illustrates the preparation of certain embodiments of the disclosure. Compounds 8d and 8e were derived from the common intermediate 17. Aryl nitrile 17 was prepared in 2 steps from 18 in 20% yield. The 2-pyrimidyl 8d was obtained from 17 in 23% yield (>95% BRSM). The 1,2,4-oxadiazole 8e was prepared via hyrdoxylamination to give the carboximidamide, which was condensed with propionic anhydride in an 80% yield for two steps.
Figure 5:
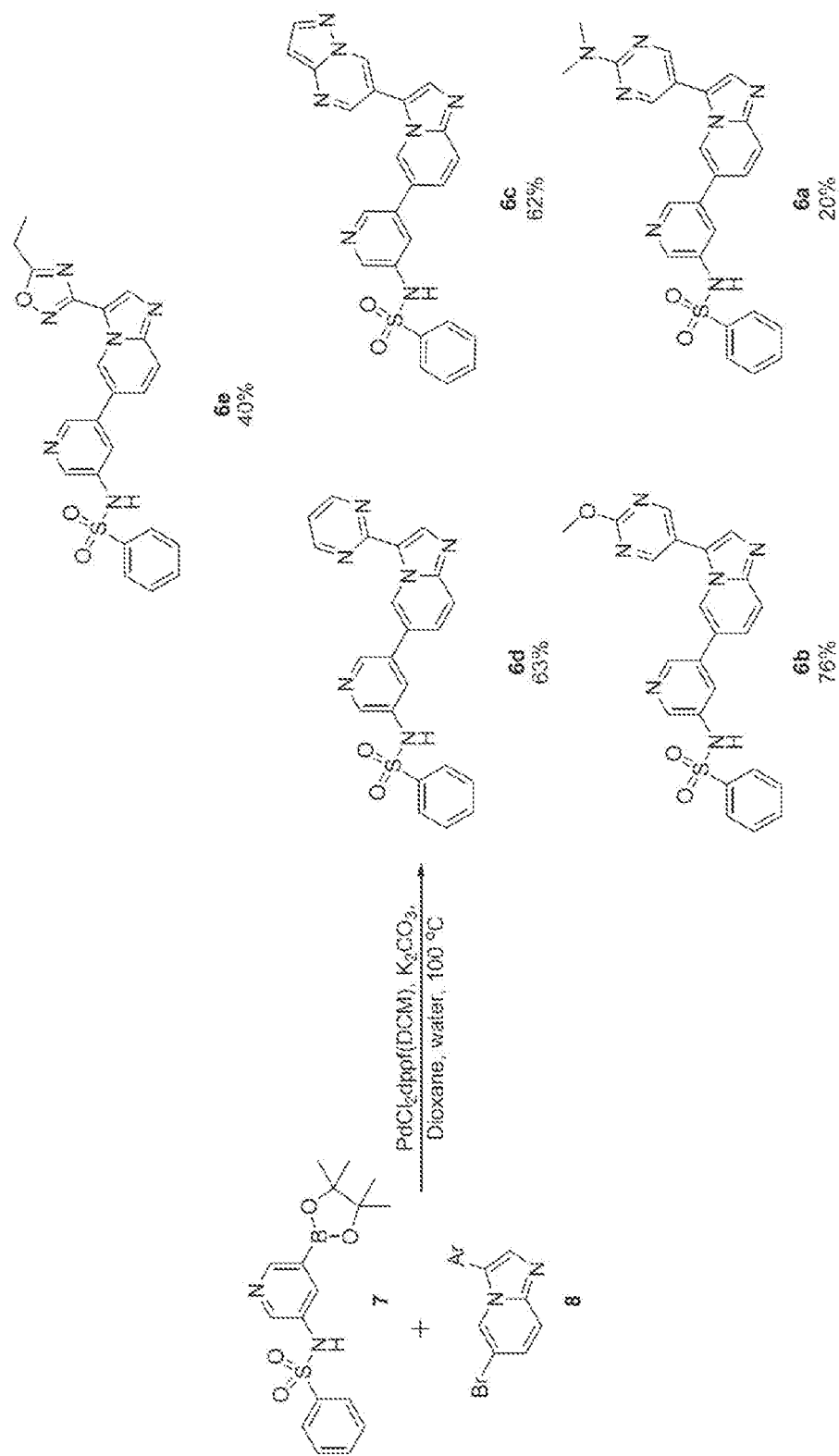
FIG. 5 illustrates the preparation of certain embodiments of the disclosure. With arylbromides 8a-8e, the compounds could be prepared through a Suzuki reaction between 7 and 8. Yields for this procedure were 20-76% with purities of >95%.
Figure 6:
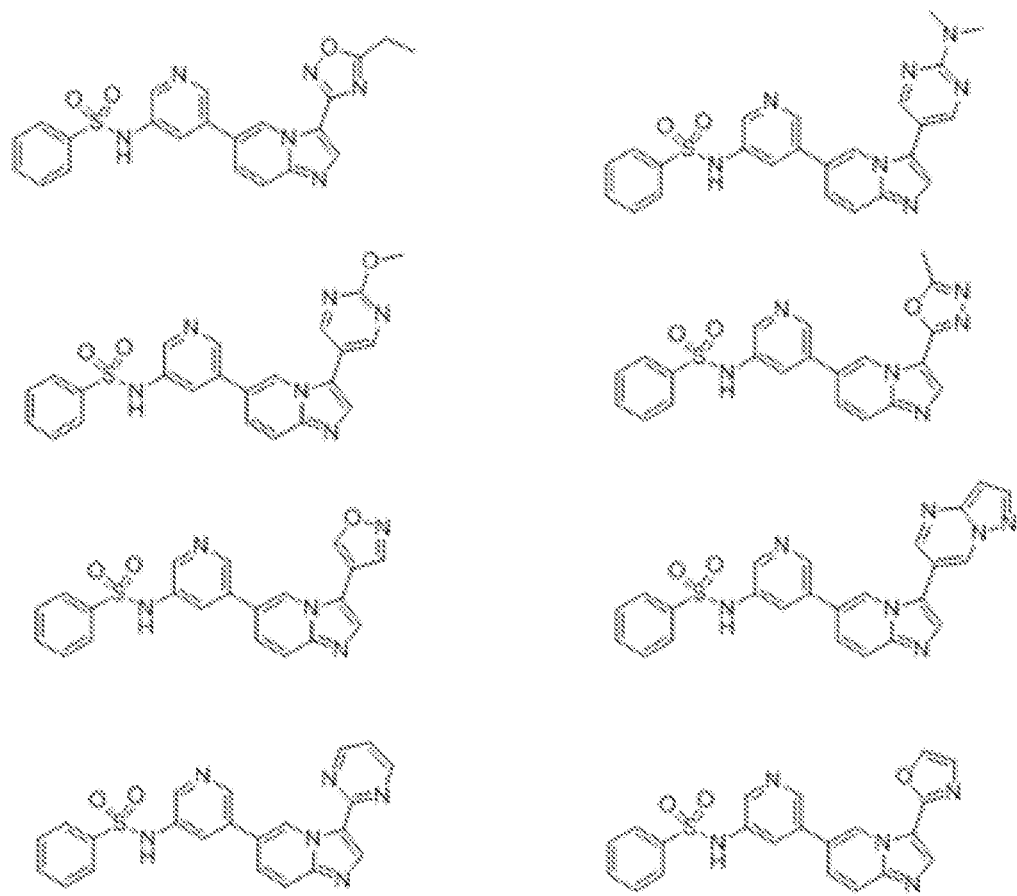
FIG. 6 illustrates additional embodiments of the disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are described.

All publications and patent documents cited in this specification are herein incorporated by reference as if each individual publication or patent document were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Certain of the compounds described herein may contain one or more asymmetric centers and may give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, tautomer forms, hydrated forms, optically substantially pure forms and intermediate mixtures.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —C(=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., $NH_2$—$CH_2$—).

"Hydroxyalkyl" refers to a hydroxy group attached through an alkyl bridge. An example of a hydroxyalkyl is hydroxyethyl, (i.e., HO—$CH_2CH_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

A "boronic acid ester" refers to a boron containing compound comprising a boron to oxygen bond. A boronic acid ester typically has two boron oxygen bonds. Examples include boronic acid 1,3-propanediol ester, boronic acid catechol ester, boronic acid pinacol ester (4,4,5,5-tetramethyl-1,3,2-dioxaborolane), boronic acid neopentylglycol ester (5,5-dimethyl-1,3,2-dioxaborinane), boronic acid hexylene glycol (2-methyl-2,4-pentanediol) ester, boronic acid N-methyliminodiacetic acid ester, boronic acid diisopropyl ester, boronic acid N-butyldiethanolamine ester, boronic acid N-phenyldiethanolamine ester.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skilled in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Pyridin-3-yl-imidazolpyridine Derivatives

In certain embodiments, the N-(5-(imidazo[1,2-a]pyridin-6-yl)pyridin-3-yl)sulfonamide derivatives are those having the following formula:

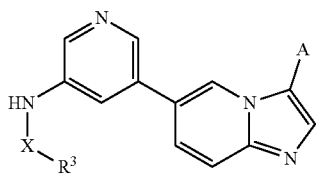

Formula I derivatives, esters, prodrugs, or salts thereof wherein
X is $SO_2$, or SO;
A is aryl or heteroaryl, wherein A is optionally substituted with one or more, the same or different, $R^{10}$;
$R^3$ is alkyl, benzyl, carbocyclyl, aryl, or heterocyclyl, wherein $R^3$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, A is pyrimidin-2-yl, pyrimidin-5-yl, pyrazolo[1,5-a]pyrimidin-6-yl or 1,2,4-oxadiazol-3-yl, optionally substituted.

In certain embodiments, the N-(5-(imidazo[1,2-a]pyridin-6-yl)pyridin-3-yl)sulfonamide derivatives are those having the following formula:

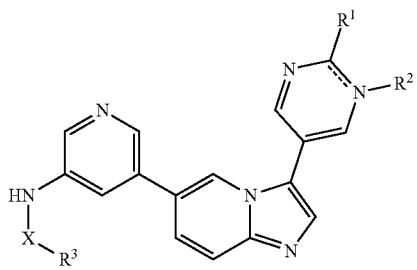

Formula IA derivatives, esters, prodrugs, or salts thereof wherein
X is $SO_2$, or SO;

$R^1$ and $R^2$ come together to form a heterocyclyl optionally substituted with one or more, the same or different, $R^{10}$; or the broken line is a double bond and $R^2$ is absent and $R^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein $R^1$ and $R^2$ are optionally substituted with one or more, the same or different, $R^{10}$;
$R^3$ is alkyl, benzyl, carbocyclyl, aryl, or heterocyclyl, wherein $R^3$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

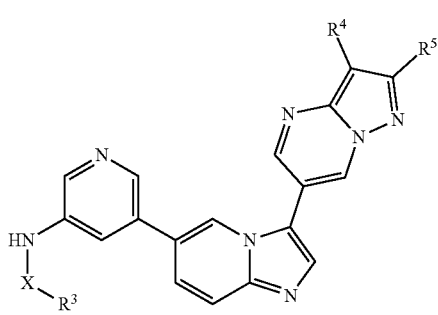

Formula IB derivatives, esters, prodrugs, or salts thereof wherein
X is $SO_2$, or SO;
$R^4$ and $R^5$ are individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein $R^4$ and $R^5$ are optionally substituted with one or more, the same or different, $R^{10}$; $R^3$ is alkyl, benzyl, carbocyclyl, aryl, or heterocyclyl, wherein $R^3$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

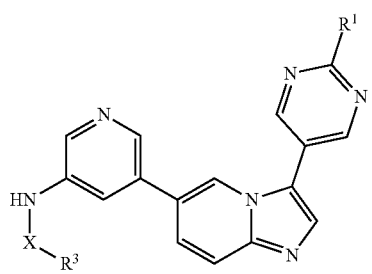

Formula IC derivatives, esters, prodrugs, or salts thereof wherein
X is $SO_2$, or SO;

$R^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, benozyl, benzyl, carbocyclyl, aryl, or heterocyclyl, wherein $R^1$ is optionally substituted with one or more, the same or different, $R^{10}$;

$R^3$ is alkyl, benzyl, carbocyclyl, aryl, or heterocyclyl, wherein $R^3$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

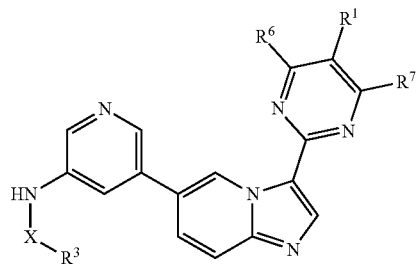

Formula ID derivatives, esters, prodrugs, or salts thereof wherein
X is $SO_2$, or SO;

$R^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, benozyl, benzyl, carbocyclyl, aryl, or heterocyclyl, wherein $R^1$ is optionally substituted with one or more, the same or different, $R^{10}$;

$R^6$ and $R^7$ are individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, benozyl, benzyl, carbocyclyl, aryl, or heterocyclyl, wherein $R^6$ and $R^7$ are optionally substituted with one or more, the same or different, $R^{10}$;

$R^3$ is alkyl, benzyl, carbocyclyl, aryl, or heterocyclyl, wherein $R^3$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

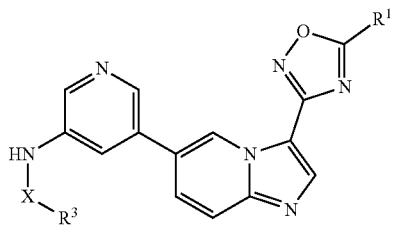

Formula IE derivatives, esters, prodrugs, or salts thereof wherein

X is SO$_2$, or SO;

R$^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein R$^1$ is optionally substituted with one or more, the same or different, R$^{10}$;

R$^3$ is alkyl, benzyl, carbocyclyl, aryl, or heterocyclyl, wherein R$^3$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

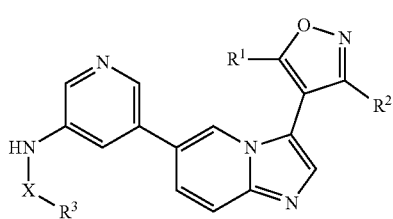

Formula IF derivatives, esters, prodrugs, or salts thereof wherein

X is SO$_2$, or SO;

R$^1$ and R$^2$ are individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein R$^1$ and R$^2$ are optionally substituted with one or more, the same or different, R$^{10}$;

R$^3$ is alkyl, benzyl, carbocyclyl, aryl, or heterocyclyl, wherein R$^3$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

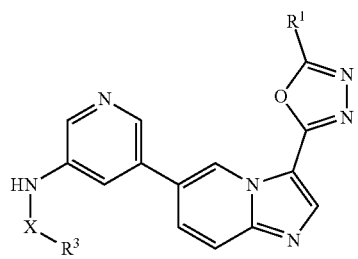

Formula IG derivatives, esters, prodrugs, or salts thereof wherein

X is SO$_2$, or SO;

R$^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein R$^1$ is optionally substituted with one or more, the same or different, R$^{10}$;

R$^3$ is alkyl, benzyl, carbocyclyl, aryl, or heterocyclyl, wherein R$^3$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, the N-(5-(imidazo[1,2-a]pyridin-6-yl)pyridin-3-yl)sulfonamide derivatives are those having the following formula:

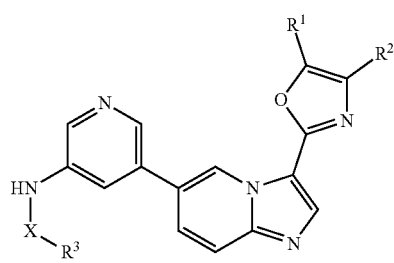

Formula IF derivatives, esters, prodrugs, or salts thereof wherein
X is SO$_2$, or SO;

R$^1$ and R$^2$ are individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benozyl, benzyl, carbocyclyl, aryl, or heterocyclyl, wherein R$^1$ and R$^2$ are optionally substituted with one or more, the same or different, R$^{10}$;

R$^3$ is alkyl, benzyl, carbocyclyl, aryl, or heterocyclyl, wherein R$^3$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In one preferred embodiment, the compound of Formula I is selected from any one of

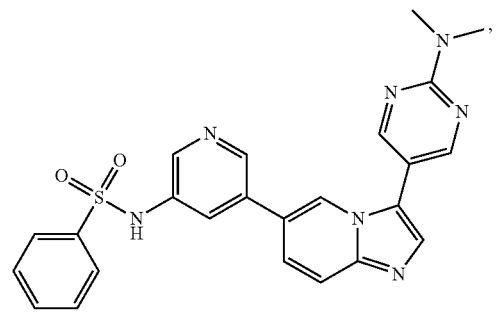

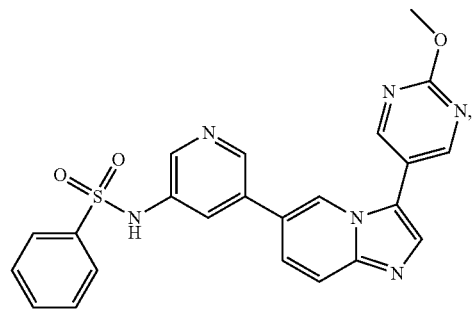

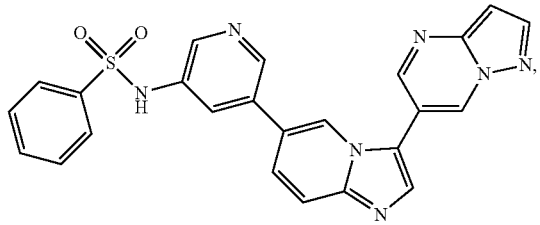

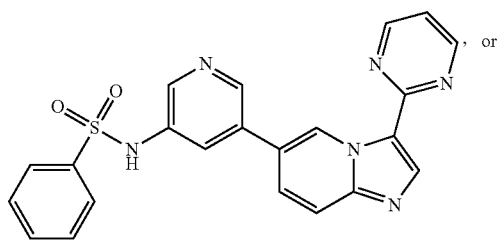

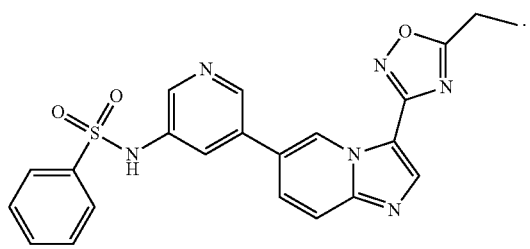

Methods of Making N-(5-(imidazo[1,2-a]pyridin-6-yl)pyridin-3-yl)sulfonamide Derivatives In certain embodiments, the disclosure relates to methods of making N-(5-(imidazo[1,2-a]pyridin-6-yl)pyridin-3-yl)sulfonamide derivatives, e.g., a compound having the following formula:

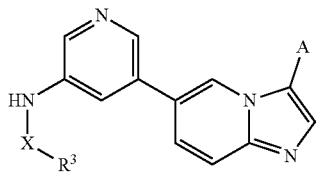

Formula I derivatives, esters, prodrugs, or salts thereof, wherein said method comprises mixing a compound of formula II

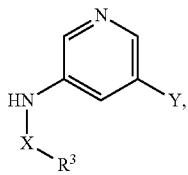

Formula II wherein, Y is a boron ester,
with a compound of formula III,

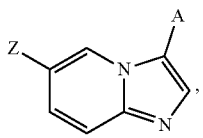

Formula III wherein, Z is a halogen,
under conditions such that a compound of Formula I is formed,
wherein,
X is $SO_2$, or SO;
A is aryl or heteroaryl, wherein A is optionally substituted with one or more, the same or different, $R^{10}$;
$R^3$ is alkyl, benzyl, carbocyclyl, aryl, or heterocyclyl, wherein $R^3$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethyl sulfamoyl, N,N-diethylsulfamoyl, N-methyl-N-ethylsulfamoyl, benozyl, benzyl, carbocyclyl, aryl, or heterocyclyl.

In certain embodiments, A is selected from:

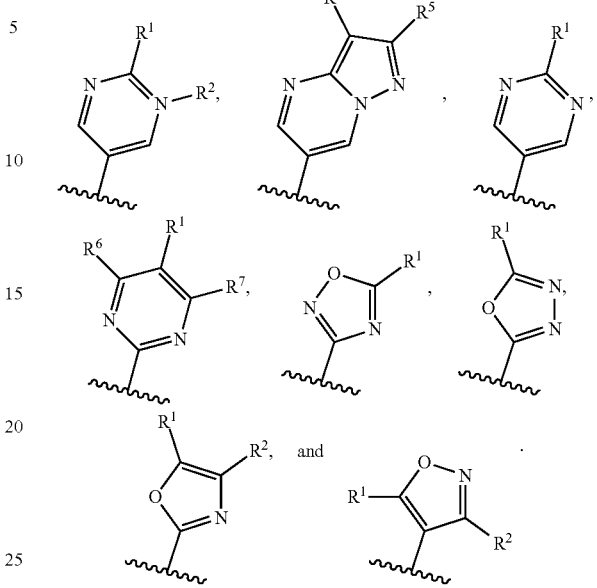

Methods of Use

In certain embodiments, the disclosure relates to methods of treating PI3K associated diseases or conditions comprising administering an effective amount of a compound disclosed herein to a subject in need thereof. In certain embodiments, the subject is at risk of, exhibiting symptoms of, suffering from or diagnosed with respiratory disease, immunological disease, cancer, or a hematological malignancy.

In some embodiments, the disorder treated by the methods or compounds disclosed herein is a cancer. In some embodiments, the cancer is a solid or soft tissue tumor (e.g., a carcinoid, carcinoma or sarcoma), a hematopoietic tissue tumor (e.g., a heme malignancy), or a metastatic lesion, e.g., a metastatic lesion of any of the cancers or tumors disclosed herein. In one embodiment, the cancer is metastatic cancer to the bone.

In one embodiment, the cancer treated by the methods or compounds disclosed herein is a soft tissue tumor, a heme malignancy, or a hematological cancer. In one embodiment, the cancer is acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus type 1 (HTLV-1) leukemia/lymphoma, AIDS-related lymphoma, adult T-cell lymphoma, acute lymphoblastic leukemia (ALL), T-cell acute lymphoblastic leukemia, B-cell acute lymphoblastic leukemia, chronic lymphocytic leukemia, or multiple myeloma (MM). In one embodiment, the cancer is leukemia or lymphoma. In one embodiment, the leukemia is B-cell acute lymphoblastic leukemia (B-ALL), acute myeloid leukemia (AML), acute lymphoblastic leukemia, chronic myeloid leukemia, hairy cell leukemia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is diffuse large B-cell lymphoma, B-cell immunoblastic lymphoma, small non-cleaved cell or Burkitt lymphoma, human lymphotropic virus-type 1 (HTLV-1) leukemia/lymphoma, adult T-cell lymphoma, Hodgkin disease, or non-Hodgkin lymphomas, or a metastatic lesion thereof.

In one embodiment, the cancer treated by the methods or compounds disclosed herein is a solid tumor (e.g., a carcinoid, carcinoma or sarcoma), or a metastatic lesion thereof. In one embodiment, the cancer is a lung cancer (e.g., non-small cell lung cancer or small cell lung cancer); a skin cancer; a melanoma; a prostate cancer; a glioblastoma; an endometrial cancer; a pancreatic cancer (e.g., pancreatic adenocarcinoma (e.g., pancreatic ductal adenocarcinoma (PDA)); a renal cell carcinoma; a colorectal cancer; a breast cancer (e.g., triple negative breast cancer); a thyroid cancer; a sarcoma, a liver or hepatocellular cancer (HCC), a head and neck cancer, a cervical or vulvar cancer, an esophageal cancer, a gastric cancer, an adrenal cancer, or an ovarian cancer, or a metastatic lesion thereof. In one embodiment, the solid tumor is prostate cancer, breast cancer, or a glioblastoma, or a metastatic lesion thereof.

In some embodiments, the cancer or tumor treated is a solid, fibrotic tumor chosen from one or more of pancreatic (e.g., pancreatic adenocarcinoma or pancreatic ductal adenocarcinoma), breast, colorectal, colon, lung (e.g., a small or non-small cell lung cancer), skin, ovarian, prostate, cervix, gastrointestinal (e.g., carcinoid or stromal), stomach, head and neck, kidney, brain cancer, or a metastatic lesion thereof.

In some embodiments, the cancer or tumor treated using the methods or compounds disclosed herein is a cancer or tumor chosen from one or more of the head, neck, nasal cavity, paranasal sinuses, nasopharynx, oral cavity, oropharynx, larynx, hypopharynx, salivary glands, paragangliomas, pancreas, stomach, skin, esophagus, endometrium, liver and biliary tree, bone, intestine, colon, rectum, ovaries, prostate, lung, breast, lymphatic system, blood, bone marrow central nervous system, brain, or a metastatic lesion thereof.

In one embodiment, the method further comprises administration of one or more therapeutic agents selected from chemotherapeutic agents, cytotoxic agents, and radiation. In one embodiment, the compound is administered in combination with an mTOR inhibitor.

In some embodiments, a method of reducing one or more activities of a pro-tumor immune cell in a subject having a cancer is provided. The method includes administering to the subject a PI3K inhibitor or a compound as described herein in an amount sufficient to reduce or inhibit the one or more activities of the pro-tumor immune cell.

In some embodiments, the pro-tumor immune cell is a T-cell, an M2 macrophage, a stromal cell, a dendritic cell, an endothelial cell, or a myeloid cell. In one embodiment, the myeloid cell is a tumor associated suppressive myeloid cell. In one embodiment, the tumor associated suppressive myeloid cell is a tumor associated macrophage (TAM), a myeloid derived suppressor cell (MDSC), a monocytic immature myeloid cell (iMc), or a granulocytic iMc/neutrophil.

In certain embodiments, the subject has, or is identified as having, a decrease in numbers of pro-tumor immune cells in a tumor microenvironment, compared to a reference value, after administration of the PI3K inhibitor or a compound as described herein.

In certain embodiments, the amount of the administered is sufficient to produce a decrease in numbers of pro-tumor immune cells in a tumor microenvironment, compared to a reference value, after administration of the PI3K inhibitor or a compound as described herein.

In certain embodiments, the subject has, or is identified as having, increased activity of anti-tumor immune cells, compared to a reference value, after administration of the PI3K inhibitor or a compound as described herein.

In certain embodiments, the amount of the PI3K inhibitor or a compound as described herein is sufficient to produce increased activity of anti-tumor immune cells, compared to a reference value, after administration of the PI3K inhibitor or the compound as described herein.

In certain embodiments, the subject has, or is identified as having, increased infiltration of anti-tumor immune cells into a tumor microenvironment, compared to a reference value, after administration of the PI3K inhibitor or a compound as described herein.

In certain embodiments, the amount of PI3K inhibitor is sufficient to produce increased infiltration of anti-tumor immune cells into a tumor microenvironment, compared to a reference value, after administration of the PI3K inhibitor or a compound as described herein.

In certain embodiments, the subject has, or is identified as having, an increase in number of anti-tumor immune cells in a tumor microenvironment, compared to a reference value, after administration of the PI3K inhibitor or a compound as described herein.

In certain embodiments, the amount of PI3K inhibitor is sufficient to produce an increase in number of anti-tumor immune cells in a tumor microenvironment, compared to a reference value, after administration of the PI3K inhibitor or a compound as described herein.

In certain embodiments, the cancer is a CLL. In some embodiments, the tumor microenvironment is a CLL proliferation center.

In certain embodiments, the subject has, or is identified as having, reduced tumor volume, compared to a reference value, after administration of the PI3K inhibitor or a compound as described herein.

In certain embodiments, the amount of the PI3K inhibitor or a compound as described herein is sufficient to produce reduced tumor volume, compared to a reference value, after administration of the PI3K inhibitor or the compound as described herein.

In certain embodiments, the amount of the PI3K inhibitor or a compound as described herein is sufficient to produce a reduction of at least 10%, 20%, 30%, 40%, 50%, or 60% in tumor volume, compared to a reference value, after administration of the PI3K inhibitor or the compound as described herein.

In certain embodiments, the subject has, or is identified as having, an increased level of apoptosis in the cancer cells, compared to a reference value, after administration of the PI3K inhibitor or a compound as described herein.

In certain embodiments, the amount of PI3K inhibitor is sufficient to produce an increased level of apoptosis in the cancer cells, compared to a reference value, after administration of the PI3K inhibitor or a compound as described herein.

In certain embodiments, the subject has, or is identified as having, a 10%, 20%, 30%, 40%, or 50% increase in apoptosis in the cancer cells, compared to a reference value, after administration of the PI3K inhibitor or a compound as described herein.

In certain embodiments, the cancer is, or is determined to be, a solid tumor (e.g., a cancer chosen from lung cancer, breast cancer, colon cancer, or glioblastoma).

In another aspect, the invention features a method of treating a solid tumor, comprising administering to a subject in need thereof an effective amount of a PI3K inhibitor or a compound as described either prior to administering the radiation therapy, after administering radiation therapy, or at the same time as administering radiation therapy.

In certain embodiments, the cancer is selected from one or more of: a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma. In certain embodiments, the solid tumor is a lung tumor, breast tumor, colon tumor, brain tumor, bone tumor, glioblastoma, or a metastatic lesion thereof. In one embodiment, the combination of radiation and/or PI3K inhibition is such that accumulation of tumor supporting-myeloid cells into the radiated tumor is reduced or prevented, thus impairing tumor regrowth following radiation therapy.

In some embodiments, the disorder treated by the methods or compounds disclosed herein is an inflammatory disease or an immune disease. In one embodiment, the inflammatory disease or the immune disease is asthma, emphysema, allergy, dermatitis, arthritis (e.g., rheumatoid arthritis), psoriasis, lupus erythematosus, graft versus host disease, inflammatory bowel disease, eczema, scleroderma, Crohn's disease, or multiple sclerosis. In one embodiment, the disorder is rheumatoid arthritis. In one embodiment, the disorder is rheumatoid arthritis, and the amount of the compound is effective to ameliorate one or more symptoms associated with rheumatoid arthritis, wherein the symptom associated with rheumatoid arthritis is independently a reduction in the swelling of the joints, a reduction in serum anti collagen levels, a reduction in bone resorption, a reduction in cartilage damage, a reduction in pannus, or a reduction in inflammation.

In some embodiments, the disorder treated by the methods or compounds disclosed herein is a respiratory disease. In one embodiment, the respiratory disease is asthma, chronic obstructive pulmonary disease (COPD), chronic bronchitis, emphysema, or bronchiectasis. In one embodiment, the disorder is asthma.

In certain embodiments, a method is provided for selectively inhibiting a PI3 kinase isoform over PI3 kinase alpha or beta isoform wherein the inhibition takes place in a subject suffering from a respiratory disease. In one embodiment, the respiratory disease is asthma, chronic obstructive pulmonary disease (COPD), chronic bronchitis, emphysema, or bronchiectasis. In one embodiment, the respiratory disease is asthma. In one embodiment, the respiratory disease is COPD.

In some aspects, the present disclosure provides a method of treating (e.g., ameliorating, preventing, and/or managing) a pulmonary or respiratory disease in a subject, comprising administering to a subject in need thereof by inhalation a therapeutically or prophylactically effective amount of a PI3K inhibitor or a compound as described herein or a pharmaceutically acceptable form thereof.

In some aspects, this disclosure provides a method of eliciting a prolonged anti-inflammatory effect in a lung in a subject suffering from a pulmonary or respiratory disease, comprising administering to the subject by inhalation a therapeutically or prophylactically effective amount of the PI3K inhibitor or a compound as described herein or a pharmaceutically acceptable form thereof, wherein the compound is retained in lung for a period longer than what is provided by oral administration.

In some embodiments, the compound is retained in the lung for a period that is sufficient to administer the compound once a day, twice a day, three times a day, four times a day, five times a day, or once every two day.

In some embodiments, the compound is retained in lung for about 1 hour, about 3 hours, about 6 hours, about 12 hours, about 24 hours, about 48 hours, or about 72 hours longer than what is provided by oral administration.

In some embodiments, administering an effective amount of the compound does not result in, or results in reduced, one or more common side effects associated with treatment of pulmonary or respiratory diseases. In some embodiments, the common side effect associated with treatment of pulmonary or respiratory diseases is oral candidiasis, thrush, dysphonia, reflex cough, bronchospasm, poor growth, decreased bone density, disseminated varicella infection, easy bruising, cataracts, glaucoma, adrenal gland suppression, stomach upset, headache, liver test abnormalities, skin rashes, Churg Strauss syndrome, bad taste in month, cough, itching, sore throat, sneezing, stuffy nose, shortness of breath, wheezing, viral illness, upper respiratory tract infections, sinusitis, feeling dizzy or faint, hives, changes in voice, swelling of the tongue, or difficulty in swallowing.

In some embodiments, administering an effective amount of the compound reduces one of more of symptoms associated with pulmonary or respiratory diseases. In some embodiments, the symptom associated with pulmonary or respiratory diseases is wheezing, coughing, chest tightness, shortness of breath, difficulty in breathing, or use of accessory muscle.

In some embodiments, administering an effective amount of the compound by inhalation results in higher than about 20%, higher than about 30%, higher than about 40%, or higher than about 50% of the administered dose of the compound remaining in lung of the subject at about 24 hours after the administration.

In some embodiments, the pulmonary or respiratory disease is selected from the group consisting of pulmonary inflammation, asthma, cystic fibrosis, emphysema, chronic obstructive pulmonary disorder (COPD), chronic bronchitis, bronchiectasis, acute respiratory distress syndrome, restrictive lung diseases, respiratory tract infections, pleural cavity diseases, pulmonary vascular disease, pulmonary embolism, pulmonary arterial hypertension, pulmonary edema, pulmonary hemorrhage, and pulmonary hyperplasia.

In some embodiments, the pulmonary or respiratory disease is chronic obstructive pulmonary disorder. In some embodiments, the pulmonary or respiratory disease is asthma. In some embodiments, the asthma is selected from the group consisting of severe or refractory asthma, atopic asthma, non-atopic asthma, type 1 brittle asthma, type 2 brittle asthma, asthma attack, status asthmaticus, exercise-induced asthma, and occupational asthma.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefor such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxy groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXAMPLES

Table 1 Shows $K_i$ Data for Certain Embodiments

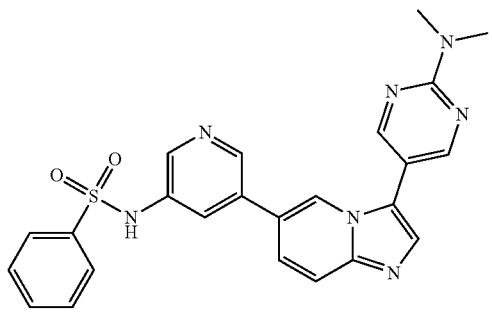

$K_i$ for PI3Kα

244 nm

6a

| | $K_i$ for PI3Kα |
|---|---|
| 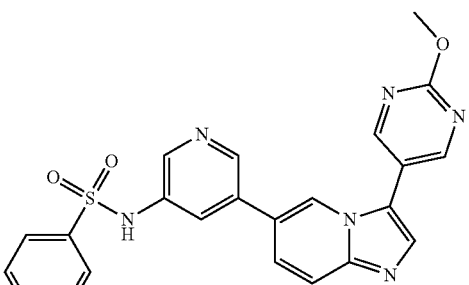 6b | 70 nm |
| 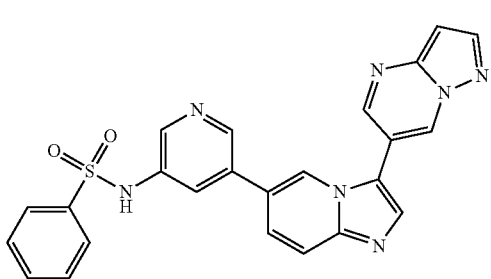 6c | 329 nm |
| 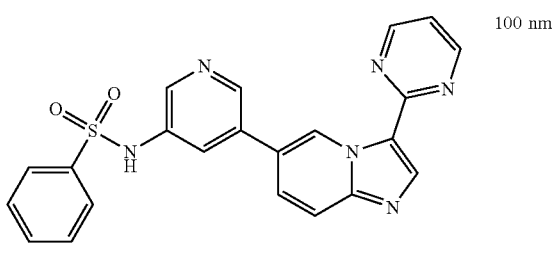 6d | 100 nm |

| | $K_i$ for PI3Kα |
|---|---|
| 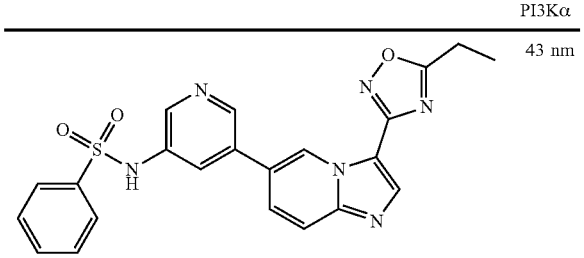 6e | 43 nm |

Summary of PI3K Kinase Assay

Enzyme optimization: After optimization, the following concentrations of Enzyme are used to compound testing:
P110alpha 1 µg/ml,
P110 beta 5 µg/ml,
P110delta 1 µg/ml,
P120 gamma 1 µg/ml Compound Testing:
1. Prepare 1.25× enzyme/substrate: mix equal volume of 2.5× enzyme (in 2.5× reaction buffer) and 2.5× substrate (final 0.05 mg/ml) (in 2.5× lipid dilution buffer);
2. Add 4 µl of 1.25× enzyme/substrate mixture to 384-well low volume white plate;
3. Add 0.1 µl of increasing concentrations of compound diluted in DMSO;
4. Incubate at r.t. for 30 min;
5. Dispense 1 µl of 250 µM ATP diluted in ddH$_2$O. The final ATP was 25 µM;
6. Incubate at r.t. for 1 h;
7. Add 5 µl of ADP-Glo with 10 mM MgCl$_2$;
8. Incubate at r.t. for 40 min;
9. Add 10 µl of kinase detection buffer;
10. Incubated at r.t. for 30 min; and
11. Read luminescence signal using Envision multilabel plate reader.

Data Analysis:
The effect of compound on kinase activity is expressed as % of control and calculated as the following equation:

% of Control=(Lum compound−Lum blank)/(Lum vehicle control−Lum blank)×100

* blank is the substrate only without enzyme, which is the background signal control.

The experiment was repeated twice on different days at triplicates per sample. All results are summarized in the Table 2 below.

Table 2 shows a summary of IC$_{50}$ values for certain embodiments in different kinase assays Summary table of IC50 (nM)

| Compound ID | p110alpha | | p110beta | | p110delta | | p120gamma | |
|---|---|---|---|---|---|---|---|---|
| | Exp. 1 | Exp. 2 | Exp. 1 | Exp. 2 | Exp. 1 | Exp. 2 | Exp. 1 | Exp. 2 |
| TK2-71pZD2-86 (6a) | 20.9 | 33.7 | 190.0 | 184.3 | 33.5 | 34.2 | 18.6 | 34.2 |
| TK2-67p3-36 (6b) | 11.7 | 12.7 | 167.5 | 186.9 | 33.5 | 27.7 | 14.9 | 27.7 |
| TK2-130p3-37 (6c) | 51.0 | 61.3 | 418.8 | 478.8 | 34.1 | 31.0 | 50.2 | 31.0 |
| TK2-94p3-47 (6d) | 8.9 | 11.5 | 27.6 | 44.9 | 10.8 | 8.5 | 7.5 | 8.5 |
| TK2-100p3-41 (6e) | 8.8 | 7.6 | 67.9 | 92.5 | 5.8 | 5.3 | 5.5 | 5.3 |
| PI 828 (Positive) | 350.9 | 349.3 | 243.7 | 242.3 | 307.8 | 202.6 | 1920.0 | 2144.5 |

Synthesis
N-(5-bromopyridin-3-yl)benzenesulfonamide (11)

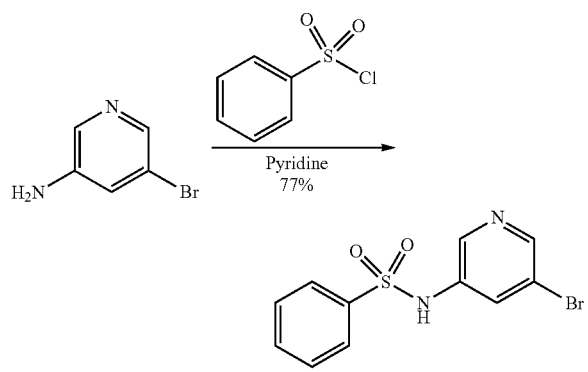

To a solution of 3-amino-5-bromopyridine (1.0 g, 5.78 mmol) in pyridine (4 mL) was added benzenesulfonyl chloride (0.82 mL, 6.36 mmol) drop-wise. The reaction mixture was stirred at r.t. for 16 h. After this time, water (10 mL) was added to the reaction mixture. The resulting crystalline solid was collected by filtration, washed with water and dried by rotovaping 2× with 20 mL methanol, 2× with 20 mL methanol DCM and 1× with DCM. The material was isolated as a beige solid (1.47 g, 81% yield). $^1$H NMR (400 MHz, CDCl$_3$/D$_6$DMSO) δ 10.52 (brs, 1H), 8.23 (s, 1H), 8.20 (s, 1H), 7.73 (d, J=7.2 Hz, 2H), 7.63 (s, 1H), 7.51 (t, J=7.2 Hz, 1H), 7.43 (t, J=7.6 Hz, 2H). $^{13}$C NMR (100 MHz, CDCl$_3$/D$_6$DMSO) δ 144.6, 138.7, 138.1, 132.1, 128.2, 128.1, 125.7. This material had spectra that were indistinguishable from the literature.

N-(5-(4,4,5,5-tetramethyl-1,3,2-dioxaborolan-2-yl)pyridin-3-yl)benzenesulfonamide (7)

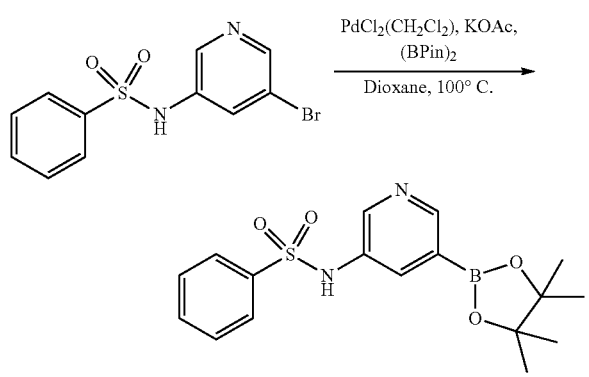

N-(5-bromopyridin-3-yl)benzenesulfonamide (1.4388 g, 4.59 mmol), 4,4,4',4',5,5,5',5'-octamethyl-2,2'-bi(1,3,2-dioxaborolane) (1.4 g, 5.51 mmol), PdCl$_2$(dppf)-DCM (150 mg, 0.18 mmol), and KOAc (1.804 g, 18.38 mmol) were combined in an oven-dried flask and placed under Ar. Dioxane (23 mL) was added and the flask was sealed and heated to 100° C. and followed by TLC. The reaction was run for ~4 hours. The reaction was concentrated and brought up in EtOAc. Celite was added and the reaction mixture was concentrated to yield a clumpy solid. This material was purified by Combiflash at 60 to 100% EtOAc in hexanes to afford0 a yellow solid. The solid was triturated with 3×15 mL of hexanes to remove the yellow color and yielded the product as a white solid (1.19 g, 72%). $^1$H NMR (400 MHz, CDCl$_3$) δ 8.69 (d, J=1.2 Hz, 1H), 8.36 (d, J=2.8 Hz, 1H), 7.92-7.91 (m, 1H), 7.78-7.75 (m, 2H), 7.54 (t, J=7.6 Hz, 1H), 7.43 (t, J=8.0 Hz, 2H), 1.33 (s, 12H). This material had spectra that were indistinguishable from the literature.

N,N-dimethyl-5-(4,4,5,5-tetramethyl-1,3,2-dioxaborolan-2-yl)pyrimidin-2-amine (10a)

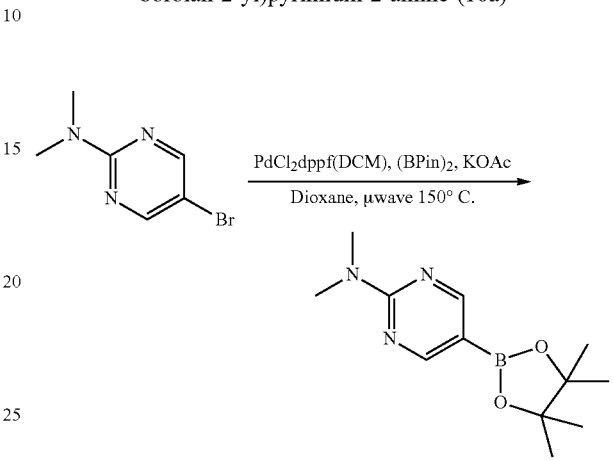

A mixture of 5-bromo-N,N-dimethylpyrimidin-2-amine (0.966 g, 4.78 mmol), 4,4,4',4',5,5,5',5'-octamethyl-2,2'-bi (1,3,2-dioxaborolane) (1.46 g, 5.74 mmol), PdCl$_2$dppf (DCM) (0.114 g, 0.14 mmol) and KOAc (1.407 g, 14.34 mmol) were placed under Ar in a 20 mL microwave flask. Anhydrous 1,2-dimethoxyethane (16 mL) was added and the flask was irradiated at 150° C. for 15 minutes. The reaction was filtered through celite, concentrated and slurried in EtOAc. The reaction was filtered through celite again and the organics were concentrated and purified by column chromatography 0 to 30% EtOAC in Hexanes. The material was isolated as a light teal solid (0.718 g, 60% yield). $^1$H NMR (400 MHz, CDCl$_3$) δ 8.59 (s, 2H), 3.21 (s, 6H), 1.31 (s, 12H). $^{13}$C NMR (100 MHz, CDCl$_3$) δ 164.1, 83.7, 77.4, 37.2, 25.2, 24.9. HRMS (EI+) m/z calculated for C$_{12}$H$_{12}$BN$_3$O$_2$ [M+H]$^+$: 250.1721, found: 250.17189.

2-Methoxy-5-(4,4,5,5-tetramethyl-1,3,2-dioxaborolan-2-yl)pyrimidine (10b)

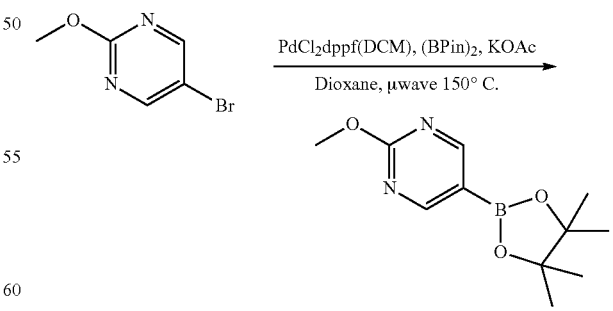

A mixture of 5-bromo-2-methoxypyrimidine (0.903 g, 4.78 mmol), 4,4,4',4',5,5,5',5'-octamethyl-2,2'-bi(1,3,2-dioxaborolane) (1.46 g, 5.74 mmol), PdCl$_2$dppf(DCM) (0.114 g, 0.14 mmol) and KOAc (1.407 g, 14.34 mmol) were placed under Ar in a 20 mL microwave flask. Anhydrous 1,2-dimethoxyethane (16 mL) was added and the flask was irradiated at 150° C. for 15 minutes. Note starting material and product are indistinguishable by TLC.

The material was concentrated and slurried in EtOAc. The material was then filtered through celite and purified by column chromatography 0 to 60% EtOAC in Hexanes. The compound was isolated as a white solid (1.01 g, 90% yield). $^1$H NMR (400 MHz, CDCl$_3$) δ 8.97 (s, 2H), 4.20 (s, 3H), 1.50 (s, 12H). $^{13}$C NMR (100 MHz, CDCl$_3$) δ 165.7, 84.5, 77.4, 55.1, 25.2, 25.0. HRMS (EI+) m/z calculated for C$_{11}$H$_{17}$BN$_2$O$_3$ [M+H]$^+$: 237.1405, found: 237.14008.

6-(4,4,5,5-Tetramethyl-1,3,2-dioxaborolan-2-yl) pyrazolo[1,5-a]pyrimidine (10c)

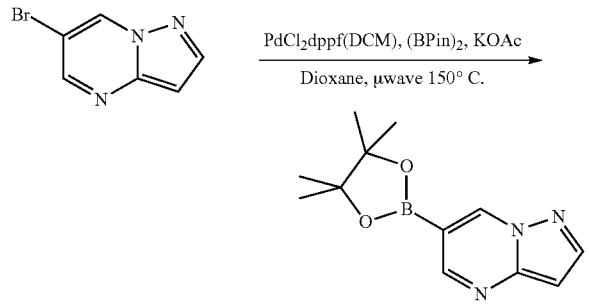

A mixture of 6-bromopyrazolo[1,5-a]pyrimidine (0.947 g, 4.78 mmol), 4,4,4',4',5,5,5',5'-octamethyl-2,2'-bi(1,3,2-dioxaborolane) (1.46 g, 5.74 mmol), PdCl$_2$dppf(DCM) (0.114 g, 0.14 mmol) and KOAc (1.407 g, 14.34 mmol) were placed under Ar in a 20 mL microwave flask. Anhydrous 1,2-dimethoxyethane (16 mL) was added and the flask was irradiated in a microwave reactor at 150° C. for 15 minutes. (Note: The reaction vessel took 9 min. to reach reaction temperature). The material was concentrated and slurried in EtOAc. The material was then filtered through celite and purified by column chromatography (0 to 80% EtOAc in Hexanes). The material was isolated as a cream colored solid (0.7386 g, 63% yield). $^1$H NMR (400 MHz, CDCl$_3$) δ 8.99 (m, 1H), 8.69 (d, J=1.6 Hz, 1H), 8.16 (d, J=2.0 Hz, 1H), 6.68 (dd, J=0.8, 2.0 Hz, 1H), 1.67 (s, 12H). $^{13}$C NMR (100 MHz, CDCl$_3$) δ 153.6, 149.2, 146.2, 141.9, 97.2, 84.8, 77.4, 23.0. HRMS (EI+) m/z calculated for C$_{12}$H$_{17}$BN$_3$O$_2$ [M+H]$^+$: 246.1408, found: 246.14066.

6-Bromo-3-iodoimidazo[1,2-a]pyridine (9)

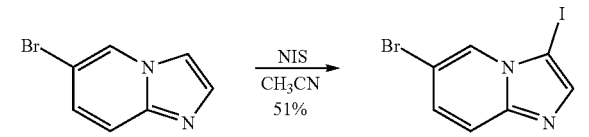

To a solution of 6-bromoimidazo[1,2-a]pyridine (5 g, 25.4 mmol) in CH$_3$CN (139 mL) was added NIS (6.85 g, 30.5 mmol). The reaction was stirred at r.t. for 1 hour and the reaction was concentrated. The residue was diluted with DCM (140 mL) and washed with 100 mL of 10% NaOH, 100 mL of saturated thiosulfate solution, and then 100 mL of water. The organic layer was dried over MgSO$_4$, filtered and concentrated. The material was isolated as a beige solid (4.163 g, 51% yield). $^1$H NMR (400 MHz, CDCl$_3$) δ 8.28-8.27 (m, 1H), 7.69 (s, 1H), 7.51 (dd, J=1.2, 12.8 Hz, 1H), 7.29 (dd, J=2.8, 12.8 Hz, 1H). This material had spectra that were indistinguishable from the literature.

5-(6-Bromoimidazo[1,2-a]pyridin-3-yl)-N,N-dimethylpyrimidin-2-amine (8a)

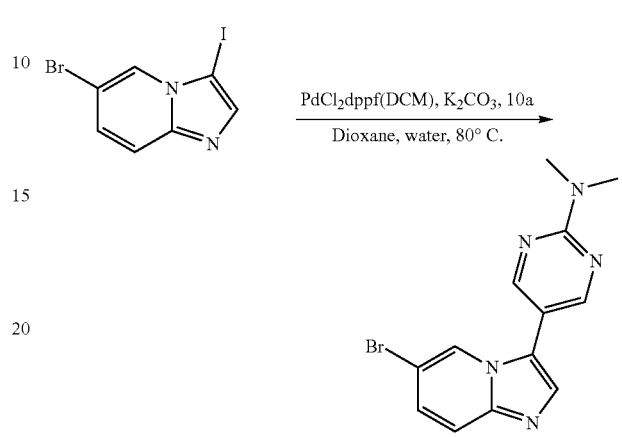

6-Bromo-3-iodoimidazo[1,2-a]pyridine (0.1 g, 0.31 mmol), N,N-dimethyl-5-(4,4,5,5-tetramethyl-1,3,2-dioxaborolan-2-yl) pyrimidin-2-amine (0.073 g, 0.31 mmol), PdCl$_2$dppf(DCM) (13 mg, 0.015 mmol) and K$_2$CO$_3$ (0.162 g, 1.174 mmol) were combined in a dried flask and placed under Ar. Dioxane (1.4 mL) and water (0.47 mL) were added and the reaction was heated to 80° C. and followed by TLC. The reaction was stirred for 3.5 hours. The reaction was diluted with EtOAc and filtered through a celite plug. The plug was washed with ~125 mL of EtOAc and concentrated. The material was then purified by combiflash (0 to 10% MeOH in DCM) to give a beige solid (0.1033 g, >95% yield, the material could not be separated from pinacol and was used in the next step 14.5% contamination). $^1$H NMR (400 MHz, CDCl$_3$) δ 8.42 (s, 2H), 8.19 (s, 1H), 7.59 (s, 1H), 7.53 (d, J=9.6 Hz, 1H), 7.23 (dd, J=2.0, 9.6 Hz, 1H), 3.25 (s, 6H). $^{13}$C NMR (100 MHz, CDCl$_3$) δ 161.8, 157.6, 154.9, 133.3, 127.8, 123.3, 121.1, 119.0, 110.0, 107.8, 37.3. HRMS (EI+) m/z calculated for C$_{13}$H$_{13}$BrN$_5$ [M+H]$^+$: 318.0349, found: 318.03431.

5-(6-Bromoimidazo[1,2-a]pyridin-3-yl)-N,N-dimethylpyrimidin-2-amine (8b)

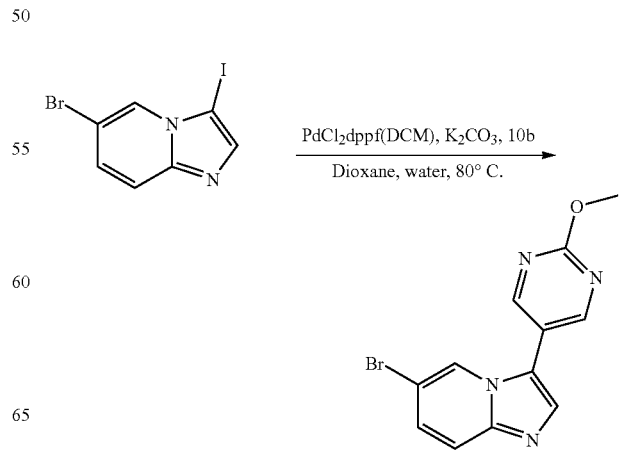

6-Bromo-3-iodoimidazo[1,2-a]pyridine (0.2 g, 0.62 mmol), 2-methoxy-5-(4,4,5,5-tetramethyl-1,3,2-dioxaborolan-2-yl)pyrimidine (0.146 g, 0.62 mmol), PdCl$_2$dppf (DCM) (26 mg, 0.031 mmol) and K$_2$CO$_3$ (0.324 g, 2.35 mmol) were combined in a dried flask and placed under Ar. Dioxane (2.8 mL) and water (0.93 mL) were added and the reaction was heated to 80° C. and followed by TLC. The reaction was diluted with EtOAc and filtered through a celite plug. The plug was washed with ~125 mL of EtOAc and concentrated. The material was then purified by combiflash (0 to 10% MeOH in DCM) to give a beige solid (0.1219 g, 65%, the material could not be separated from pinacol and was used in the next step 7.3% contamination). $^1$H NMR (400 MHz, CDCl$_3$) δ 8.69 (s, 2H), 8.22 (m, 1H), 7.69 (s, 1H), 7.59 (dd, J=0.8, 9.6 Hz, 1H), 7.30 (dd, J=2.0, 9.6 Hz, 1H), 4.10 (s, 3H). $^{13}$C NMR (100 MHz, CDCl$_3$) δ 165.5, 158.8, 145.0, 134.0, 128.4, 122.8, 119.3, 119.1, 116.9, 108.2, 55.4. HRMS (EI+) m/z calculated for C$_{12}$H$_{10}$BrN$_4$O [M+H]$^+$: 305.0032, found: 305.00286.

6-(6-Bromoimidazo[1,2-a]pyridin-3-yl)pyrazolo[1,5-a]pyrimidine (8c)

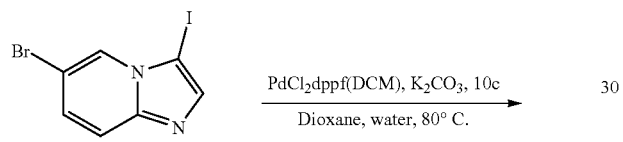

6-Bromo-3-iodoimidazo[1,2-a]pyridine (0.1 g, 0.31 mmol),6-(4,4,5,5-tetramethyl-1,3,2-dioxaborolan-2-yl)pyrazolo[1,5-a]pyrimidine (0.076 g, 0.31 mmol), PdCl$_2$dppf (DCM) (13 mg, 0.015 mmol) and K$_2$CO$_3$ (0.162 g, 1.174 mmol) were combined in a flask and placed under Ar. Dioxane (1.4 mL) and water (0.47 mL) were added and the reaction was heated to 80° C. and followed by TLC. The reaction was diluted with EtOAc and filtered through a celite plug. The plug was washed with ~125 mL of EtOAc and concentrated. The material was then purified by combiflash (0 to 10% MeOH in DCM) to give a beige solid (0.042 g, 41% yield). NMR (400 MHz, CD$_3$OD/CDCl$_3$) δ 8.99 (d, J=1.6 Hz, 1H), 8.62 (d, J=2.4 Hz, 1H), 8.39 (d, J=0.8 Hz, 1H), 8.22 (d, J=2.4 Hz, 1H), 7.76 (s, 1H), 7.59 (d, J=9.6 Hz, 1H), 7.42-7.39 (m, 1H), 6.81 (s, 1H). $^{13}$C NMR (100 MHz, CD$_3$OD/CDCl$_3$) δ 186.7, 149.2, 147.4, 146.1, 144.8, 134.2, 133.8, 129.5, 123.2, 118.3, 110.0, 108.7, 97.6. HRMS (EI+) m/z calculated for C$_{13}$H$_9$BrN$_5$ [M+H]$^+$: 314.0036, found: 314.00299.

N'-(5-bromopyridin-2-yl)-N,N-dimethylformimidamide (17-1)

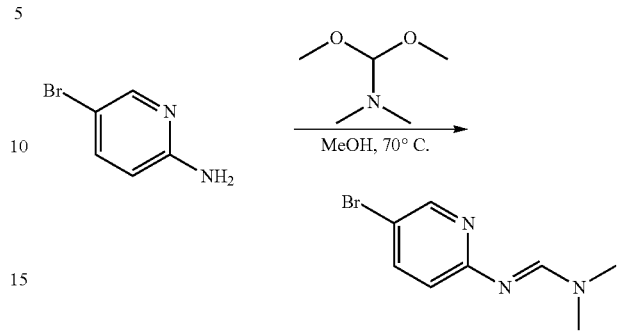

To a solution of 5-bromopyridin-2-amine (1.7 g, 9.83 mmol) in MeOH (10 mL) was added 1,1-dimethoxy-N,N-dimethylmethanamine (1.6 mL, 11.9 mmol). The reaction was heated at 70° C. for 6 hours. The reaction was concentrated and the mixture was recrystallized from ~20 mL of hexanes heated to reflux with a heat gun. Crystals were a yellow solid (1.8318 g, 82%). $^1$H NMR (400 MHz, CDCl$_3$) δ 8.38 (s, 1H), 8.25 (dd, J=0.8, 2.8 Hz, 1H), 7.60 (dd, J=2.8, 8.8 Hz, 1H), 6.83 (dd, J=0.4, 8.4 Hz, 1H), 3.09 (s, 3H), 3.07 (2, 3H). Spectrum was indistinguishable from the literature.

6-Bromoimidazo[1,2-a]pyridine-3-carbonitrile (17)

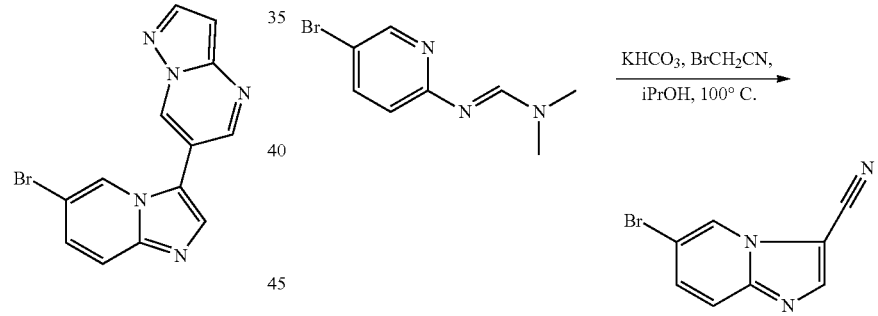

To a mixture of N'-(5-bromo-2-pyridinyl)-N,N-dimethylimidoformamide (0.9274 g, 4.07 mmol) in i-PrOH (18.5 mL) was added bromoacetonitrile (0.334 mL, 4.80 mmol) followed by NaHCO$_3$ (0.59 g, 5.90 mmol) in a sealable reaction tube. The reaction was purged with Ar, sealed and heated to 100° C. for 12 hours via microwave irradiation. The solvent evaporated from the reaction after overnight heating. The reaction was concentrated and the material was brought up in 100 mL of DCM and 50 mL of water. The organics were removed and the aqueous phase was extracted with another 100 mL of DCM. The combined organics were then dried over Na$_2$SO$_4$, filtered and concentrated. The residual brown solid was then recrystallized from EtOH to give tan crystals (0.2065 g, 23% yield). $^1$H NMR (400 MHz, CDCl$_3$) δ 8.52 (d, J=2.4 Hz, 1H), 8.15 (s, 1H), 7.68 (dd, J=0.8, 9.6 Hz, 1H), 7.53 (dd, J=2.0 Hz, 9.6 Hz, 1H). $^{13}$C NMR (100 MHz, CDCl$_3$) δ 145.8, 142.8, 132.1, 125.9, 119.3, 1106, 110.2, 110.1. Spectra were indistinguishable from the literature.

6-Bromo-3-(pyrimidin-2-yl)imidazo[1,2-a]pyridine (3c)

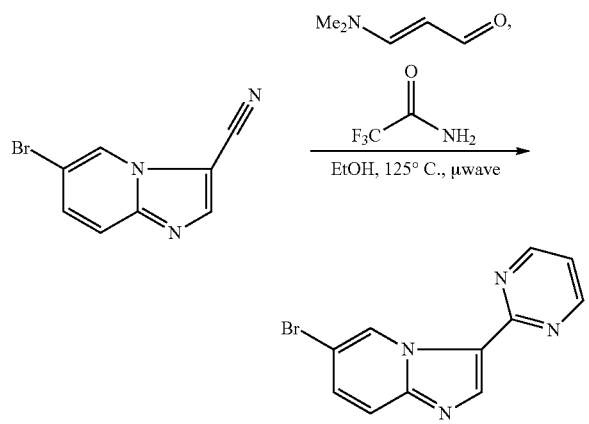

6-Bromoimidazo[1,2-a]pyridine-3-carbonitrile (0.229 g, 1.033 mmol), 2,2,2-trifluoroacetamide (0.304 g, 2.69 mmol) were placed in a microwave vial and EtOH (3.04 mL) and (dimethylamino)acrylaldehyde (0.153 mL, 1.529 mmol) were added. The vial was sealed and the reaction was irradiated to 125° C. for 2 hours. The reaction was opened, and trifluoroacetamide (0.152 g, 1.35 mmol) and (dimethylamino)acrylaldehyde (0.077 mL, 0.765 mmol) were added. The reaction was placed under Ar and irradiated to 125° C. for 3 hours. The reaction was transferred with DCM and then concentrated on rotovap. A combiflash column was run 0 to 70% EtOAc in Hexanes. Material isolated as a light yellow oil (0.0634 g, 24% yield, >95% BRSM). $^1$H NMR (400 MHz, CDCl$_3$) δ 10.14-10.13 (m, 1H), 8.79 (d, J=5.2 Hz, 2H), 8.60 (s, 1H), 7.63 (d, J=9.6 Hz, 1H), 7.43 (dd, J=2.0, 9.6 Hz, 1H), 7.13 (t, J=4.8 Hz, 1H). $^{13}$C NMR (100 MHz, CDCl$_3$) δ 158.8, 156.9, 1397, 129.5, 129.4, 128.6, 118.3, 117.8, 108.3. HRMS (EI+) m/z calculated for C$_{11}$H$_8$BrN$_4$ [M+H]$^+$: 274.9927, found: 274.99294.

3-(6-Bromoimidazo[1,2-a]pyridin-3-yl)-5-ethyl-1,2,4-oxadiazole (3d)

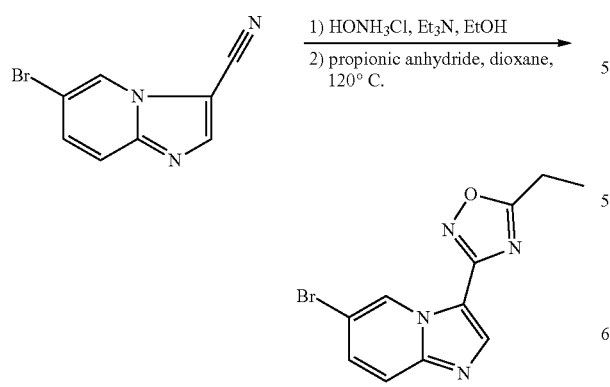

To a solution of 6-bromoimidazo[1,2-a]pyridine-3-carbonitrile (217 mg, 0.976 mmol) in EtOH (3.9 mL) were added hydroxylamine hydrochloride (0.081 g, 1.17 mmol) and Et$_3$N (0.272 mL, 2.0 mmol). The reaction was sealed and stirred at r.t. for 19 hr and then concentrated. The reaction was concentrated via rotovap and placed on high vacuum for 2 hours. The material was clean by TLC and was used in the next step.

The residue from 2-98 was placed under Ar and Dioxane (3.9 mL) was added followed by propionic anhydride (0.375 mL, 2.93 mmol). The flask was sealed, heated to 120° C. and followed by TLC. The reaction was concentrated and the material was resuspended in DCM. The mixture was then partitioned between 25 mL of DCM and 25 mL of saturated NaHCO$_3$. The layers were shaken and separated. The aqueous phase was then extracted with DCM (2×25 mL). The combined organics were dried over Na$_2$SO$_4$, filtered and concentrated. A combiflash was run 0 to 60% EtOAc in hexanes. The material was isolated as a light yellow solid (0.2279 g, 80% yield). $^1$H NMR (400 MHz, CDCl$_3$) δ 9.31 (m, 1H), 8.33 (s, 1H), 7.63 (dd, J=0.8, 9.6 Hz, 1H), 7.43 (dd, J=1.6, 9.2 Hz, 1H), 3.00 (q, J=7.6 Hz, 2H), 1.47 (t, J=7.6 Hz, 3H). $^{13}$C NMR (100 MHz, CDCl$_3$) δ 180.1, 160.7, 146.3, 138.4, 129.8, 127.9, 118.5, 114.0, 108.8, 20.1, 10.8. HRMS (EI+) m/z calculated for C$_{11}$H$_{10}$BrN$_4$O [M+H]$^+$: 293.0032, found: 293.00313.

N-(5-(3-(2-(dimethylamino)pyrimidin-5-yl)imidazo[1,2-a]pyridin-6-yl)pyridin-3-yl)benzenesulfonamide (6a)

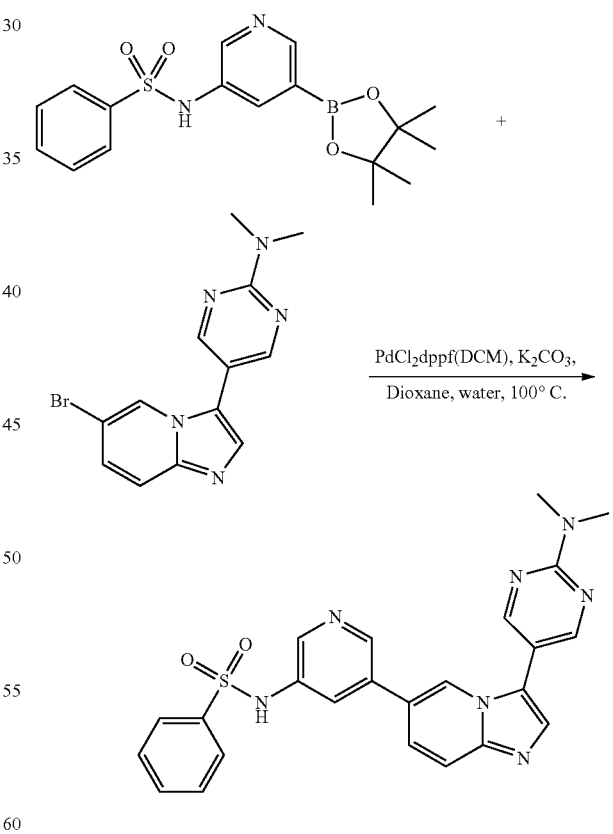

5-(6-Bromoimidazo[1,2-a]pyridin-3-yl)-N,N-dimethylpyrimidin-2-amine (0.1033 g, 0.325 mmol), N-(5-(4,4,5,5-tetramethyl-1,3,2-dioxaborolan-2-yl)pyridin-3-yl)benzenesulfonamide (0.117 g, 0.325 mmol), PdCl$_2$dppf(DCM) (13 mg, 0.015 mmol) and K$_2$CO$_3$ (0.170 g, 1.23 mmol) were combined in a dried flask and placed under Ar. Dioxane (1.5 mL) and water (0.49 mL) were added and the reaction was sealed. The reaction was heated to 100° C. and run overnight. The reaction slurry was then filtered through a celite pad and the pad was washed with ~125 mL of EtOAc. The organics were then concentrated and purified via combiflash (0 to 5% MeOH in DCM). The material was isolated as a tan residue (0.031 g, 20% yield). $^1$H NMR (400 MHz, CDCl$_3$) δ 8.51 (d, J=2.0 Hz, 1H), 8.48 (s, 2H), 8.36 (d, J=2.4 Hz, 1H), 8.19 (s, 1H), 7.83-7.78 (m, 4H), 7.69 (s, 1H), 7.58-7.52 (m, 1H), 7.45 (t, J=8.0 Hz, 1H), 7.36 (dd, J=1.6, 9.2 Hz, 1H), 3.27 (s, 6H). $^{13}$C NMR (100 MHz, CDCl$_3$) δ 161.8, 157.7, 144.2, 141.8, 139.1, 133.8, 133.5, 133.3, 129.5, 127.3, 126.6, 124.6, 123.6, 121.0, 118.8, 110.1, 77.4, 37.4. HRMS (EI+) m/z calculated for $C_{24}H_{22}N_7O_2S$ [M+H]$^+$: 472.1550, found: 472.15446. The purity was determined to be 99.16% by HPLC at 254 nm (Chiralpak ODRH, 75:25 ACN:water, 0.5 mL/min, 5.071 min).

N-(5-(3-(2-methoxypyrimidin-5-yl)imidazo[1,2-a]pyridin-6-yl)pyridin-3-yl)benzenesulfonamide (6b)

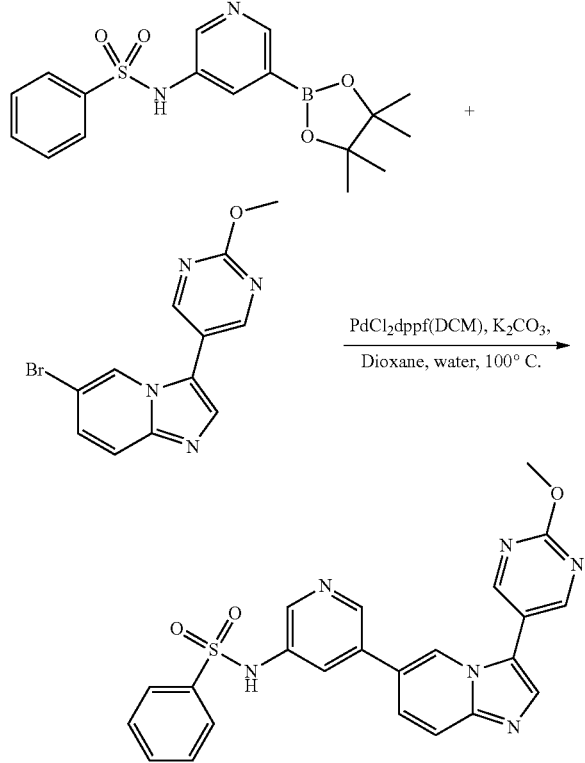

N-(5-(4,4,5,5-tetramethyl-1,3,2-dioxaborolan-2-yl)pyridin-3-yl)benzenesulfonamide (0.095 g, 0.263 mmol), 6-bromo-3-(2-methoxypyrimidin-5-yl)imidazo[1,2-a]pyridine (0.0803 g, 0.263 mmol), PdCl$_2$dppf(DCM) (10.8 mg, 0.013 mmol) and K$_2$CO$_3$ (0.138 g, 0.997 mmol) were combined in a dried flask and placed under Ar. Dioxane (1.19 mL) and water (0.40 mL) were added and the reaction was sealed and heated to 100° C. After ~one hour the top of the reaction popped off, and all solvent was found to have boiled away. The reaction was diluted with ~2 mL of EtOAc and ~2 mL of MeOH. TLC showed the reaction was complete, and the reaction slurry was then filtered through a celite pad. The pad was washed with ~125 mL of EtOAc. The organics were then concentrated and purified via combiflash (0 to 5% MeOH in DCM). Material isolated as a brown residue (0.0913 g, 76%). $^1$H NMR (400 MHz, CDCl$_3$) δ 8.78 (s, 2H), 8.52 (d, J=2.0 Hz, 1H), 8.42 (d, J=2.4 Hz, 1H), 8.27 (s, 1H), 7.85-7.79 (m, 5H), 7.54 (t, J=7.2 Hz, 1H) 7.46-7.42 (m, 3H), 4.09 (s, 3H). $^{13}$C NMR (100 MHz, CDCl$_3$) δ 165.5, 159.0, 146.0, 144.0, 141.7, 139.1, 134.7, 134.1, 133.5, 133.4, 129.4, 127.2, 126.4, 125.3, 124.2, 120.8, 119.8, 119.0, 117.3, 55.6. HRMS (EI+) m/z calculated for $C_{23}H_{19}N_6O_3S$ [M+H]$^+$: 459.1234, found: 459.12305. The purity was determined to be 99.99% by HPLC at 254 nm (Chiralpak ODRH, 75:25 ACN:water, 0.5 mL/min, 5.194 min).

N-(5-(3-(pyrazolo[1,5-a]pyrimidin-6-yl)imidazo[1,2-a]pyridin-6-yl)pyridin-3-yl)benzenesulfonamide (6c)

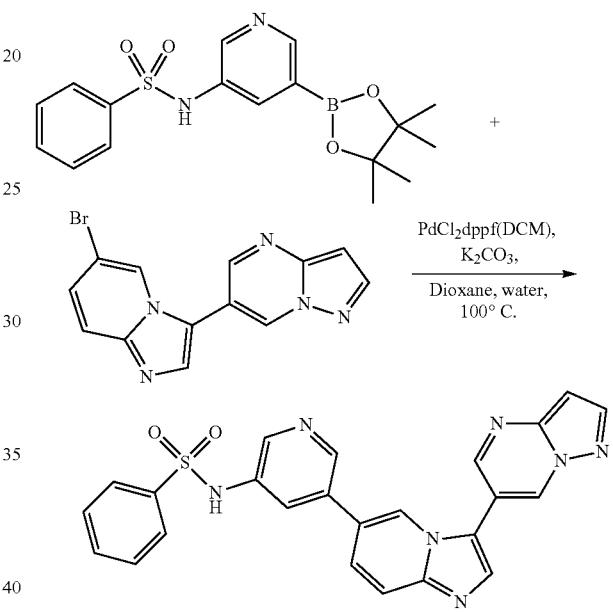

6-(6-Bromoimidazo[1,2-a]pyridin-3-yl)pyrazolo[1,5-a]pyrimidine (0.575 g, 0.183 mmol), N-(5-(4,4,5,5-tetramethyl-1,3,2-dioxaborolan-2-yl)pyridin-3-yl)benzenesulfonamide (0.066 g, 0.183 mmol), PdCl$_2$dppf(DCM) (7.47 mg, 0.00915 mmol) and K$_2$CO$_3$ (0.096 g, 0.694 mmol) were combined in a flask and placed under Ar. Dioxane (0.83 mL) and water (0.28 mL) were added and the reaction was sealed and heated to 100° C. Reaction was run for 18 hours and followed by TLC. The reaction slurry was then diluted with EtOAc, filtered through a celite pad and the pad was washed with ~125 mL of 10:1 EtOAc:MeOH. The organics were then concentrated and purified via combiflash (0 to 10% MeOH in DCM). The material was isolated as a beige solid (0.0536 g, 63% yield). $^1$H NMR (400 MHz, D$_6$DMSO) δ 10.75 (brs, 1H), 9.62-9.92 (m, 1H), 8.85-8.84 (m, 2H), 8.70 (d, J=2.0 Hz, 1H), 8.33 (d, J=2.4 Hz, 1H), 8.28 (d, J=2.4 Hz, 1H), 7.97 (s, 1H), 7.83-7.80 (m, 3H), 7.77 (t, J=2.4 Hz, 1H), 7.62-7.52 (m, 4H), 6.85 (dd, J=0.8, 2.4 Hz, 1H). $^{13}$C NMR (100 MHz, D$_6$DMSO) δ 150.3, 147.2, 145.6, 145.2, 144.0, 140.6, 139.0, 134.6, 134.5, 133.3, 133.0, 129.5, 126.8, 125.6, 124.8, 123, 122.2, 119.6, 117.8, 110.6, 96.6. HRMS (EI+) m/z calculated for $C_{24}H_{18}N_7O_2S$ [M+H]$^+$: 468.1237, found: 468.12361. The purity was determined to be 95.3135% by HPLC at 254 nm (Chiralpak ODRH, 75:25 ACN:water, 0.5 mL/min, 5.053 min).

N-(5-(3-(pyrimidin-2-yl)imidazo[1,2-a]pyridin-6-yl)pyridin-3-yl)benzenesulfonamide (6d)

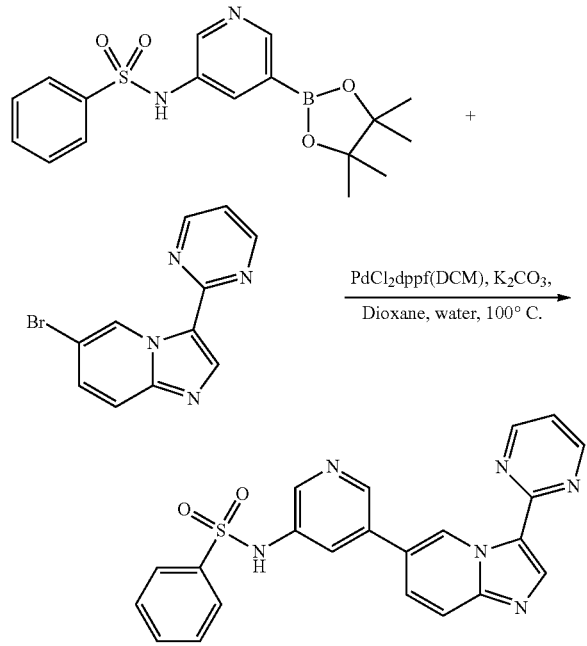

6-Bromo-3-(pyrimidin-2-yl)imidazo[1,2-a]pyridine (0.0.0634 g, 0.23 mmol), N-(5-(4,4,5,5-tetramethyl-1,3,2-dioxaborolan-2-yl)pyridin-3-yl)benzenesulfonamide (0.083 g, 0.23 mmol), PdCl$_2$dppf(DCM) (9 mg, 0.012 mmol) and K$_2$CO$_3$ (0.121 g, 0.873 mmol) were combined in a dried flask and placed under Ar. Dioxane (1.0 mL) and water (0.35 mL) were added and the reaction was sealed. The reaction was heated to 100° C. and run overnight. The reaction slurry was then filtered through a celite pad and the pad was washed with ~125 mL of EtOAc. The organics were then concentrated and purified via combiflash (0 to 5% MeOH in DCM). The material was isolated as a beige solid (0.0625 g, 63% yield). $^1$H NMR (400 MHz, CDCl$_3$/D$_6$DMSO) δ 10.78 (brs, 1H), 10.15 (s, 1H), 8.89 (d, J=4.8 Hz, 2H), 8.61 (d, J=2.0 Hz, 1H), 8.52 (s, 1H), 8.34 (d, J=2.4 Hz, 1H), 7.86-7.82 (m, 4H), 7.68-7.53 (m, 4H), 7.33 (t, J=5.2 Hz, 1H). $^{13}$C NMR (100 MHz, CDCl$_3$/D$_6$DMSO) δ 158.8, 157.5, 147.3, 143.3, 141.0, 139.7, 139.5, 133.4, 133.3, 129.5, 127.0, 126.3, 125.9, 125.0, 123.7, 118.4, 118.1, 110.0. HRMS (EI+) m/z calculated for C$_{22}$H$_{17}$N$_6$O$_2$S [M+H]$^+$: 429.1128, found: 429.11221. The purity was determined to be 96.90% by HPLC at 254 nm (Chiralpak ODRH, 75:25 ACN:water, 0.5 mL/min, 6.844 min).

N-(5-(3-(pyrimidin-2-yl)imidazo[1,2-a]pyridin-6-yl)pyridin-3-yl)benzenesulfonamide (6e)

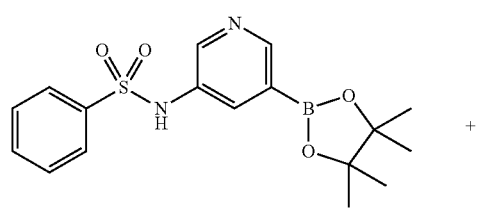

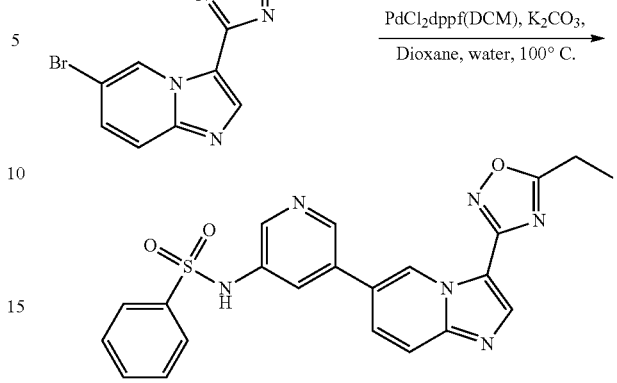

6-Bromo-3-(pyrimidin-2-yl)imidazo[1,2-a]pyridine (0.1973 g, 0.673 mmol), N-(5-(4,4,5,5-tetramethyl-1,3,2-dioxaborolan-2-yl)pyridin-3-yl)benzenesulfonamide (0.242 g, 0.673 mmol), PdCl$_2$dppf(DCM) (27 mg, 0.034 mmol) and K$_2$CO$_3$ (0.353 g, 2.55 mmol) were combined in a dried flask and placed under Ar. Dioxane (3.0 mL) and water (1.0 mL) were added and the reaction was heated to 100° C. and followed by TLC. The reaction slurry was then filtered through a celite pad and the pad was washed with ~125 mL of EtOAc. The organics were then concentrated and purified via combiflash (0 to 5% MeOH in DCM). The material was isolated as a beige solid (0.1203 g, 40% yield). $^1$H NMR (400 MHz, D$_6$DMSO) δ 10.89 (brs, 1H), 9.13 (s, 1H), 8.59 (d, J=2.0 Hz, 1H), 8.35 (d, J=2.4 Hz, 1H), 8.29 (S, 1H), 7.90-7.85 (m, 3H), 7.81 (t, J=2.0 Hz, 1H), 7.73 (dd, J=1.6, 9.2 Hz, 1H), 7.66-7.58 (m, 3H), 3.04 (q, J=7.6 Hz, 2H), 1.36 (t, J=7.6 Hz, 3H). $^{13}$C NMR (100 MHz, D$_6$DMSO) δ 180.3, 160.4, 146.6, 143.2, 140.8, 138.9, 138.2, 134.8, 133.4, 132.3, 129.6, 126.8, 126.2, 125.0, 124.2, 123.9, 118.0, 113.7, 19.5, 10.5. HRMS (EI+) m/z calculated for C$_{22}$H$_{19}$N$_6$O$_3$S [M+H]$^+$: 447.1234, found: 447.12277. The purity was determined to be 98.67% by HPLC at 254 nm (Chiralpak ODRH, 75:25 ACN:water, 0.5 mL/min, 8.012 min).

The invention claimed is:

1. A compound of the following formula,

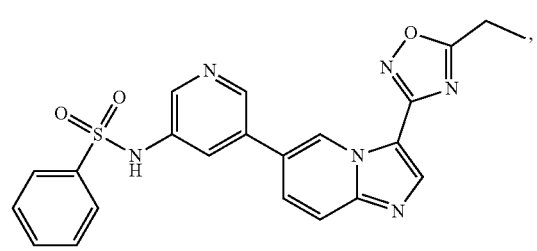 [SMILES: CCc1nc(-c2cnc3ccc(-c4cncc(NS(=O)(=O)c5ccccc5)c4)cn23)no1]

or pharmaceutically acceptable salt thereof.

2. A pharmaceutical composition comprising a compound of claim 1 and a pharmaceutically acceptable excipient.

3. The pharmaceutical composition as claimed in claim 2, wherein the pharmaceutically acceptable excipient is selected from lactose, sucrose, mannitol, triethyl citrate, or dextrose.

4. The pharmaceutical composition of claim 2 wherein the excipient is cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, or povidone.

5. The pharmaceutical composition of claim 2 wherein the excipient is a methyl or ethyl acrylate copolymer.

6. The pharmaceutical composition of claim 2 wherein the excipient is polyethylene glycol.

7. The pharmaceutical composition of claim 2 wherein the excipient is fatty acid esters of sorbitol, lauryl sulfate, gelatin, glycerin, or glyceryl monooleate.

8. The pharmaceutical composition of claim 2 wherein the excipient is silicon dioxide, titanium dioxide, or talc.

9. The pharmaceutical composition of claim 2 wherein the excipient is stearic acid, sorbic acid, magnesium stearate, or calcium stearate.

10. The pharmaceutical composition of claim 2 wherein the excipient is castor oil or mineral oil.

11. The pharmaceutical composition of claim 2 wherein the excipient is calcium phosphate.

12. The pharmaceutical composition of claim 2 wherein the excipient is starch or a carboxymethyl ether of starch.

13. The pharmaceutical composition of claim 2 wherein the excipient is iron oxide.

14. The pharmaceutical composition of claim 2 wherein the excipient is triacetin.

15. The pharmaceutical composition of claim 2 wherein the excipient is acacia gum.

16. The pharmaceutical composition of claim 2 in the form of a tablet or capsule.

17. The pharmaceutical composition of claim 2 in the form of a sugar solution.

18. The pharmaceutical composition of claim 2 in the form of an alcohol solution.

19. The pharmaceutical composition of claim 2 in the form of a physiological saline solution.

* * * * *